US008192989B2

(12) United States Patent
Yu et al.

(10) Patent No.: US 8,192,989 B2
(45) Date of Patent: *Jun. 5, 2012

(54) SOLID SURFACE FOR BIOMOLECULE DELIVERY AND HIGH-THROUGHPUT ASSAY

(75) Inventors: Lei Yu, Carlsbad, CA (US); Kenji Matsumoto, San Diego, CA (US); Shouping Ji, Oceanside, CA (US); Fusheng Du, Akron, OH (US)

(73) Assignee: Nitto Denko Corporation, Osaka (JP)

( * ) Notice: Subject to any disclaimer, the term of this patent is extended or adjusted under 35 U.S.C. 154(b) by 891 days.

This patent is subject to a terminal disclaimer.

(21) Appl. No.: 11/527,134

(22) Filed: Sep. 26, 2006

(65) Prior Publication Data

US 2007/0072171 A1    Mar. 29, 2007

Related U.S. Application Data

(63) Continuation of application No. 10/341,059, filed on Jan. 13, 2003.

(51) Int. Cl.
*C12N 15/00* (2006.01)

(52) U.S. Cl. ...................................................... 435/455

(58) Field of Classification Search .................... None
See application file for complete search history.

(56) References Cited

U.S. PATENT DOCUMENTS

| | | | |
|---|---|---|---|
| 5,264,618 A | 11/1993 | Felgner et al. | |
| 5,283,185 A | 2/1994 | Epand et al. | |
| 5,861,306 A | 1/1999 | Pugh et al. | |
| 6,025,337 A | 2/2000 | Truong et al. | |
| 6,159,591 A | 12/2000 | Beihoffer et al. | |
| 6,231,960 B1 | 5/2001 | Dyer et al. | |
| 6,319,516 B1 | 11/2001 | Huang et al. | |
| 6,319,715 B1 | 11/2001 | Luo et al. | |
| 6,376,248 B1 | 4/2002 | Hawley-Nelson et al. | |
| 6,475,994 B2 | 11/2002 | Tomalia et al. | |
| 6,544,790 B1 | 4/2003 | Sabatini | |
| 6,586,524 B2 | 7/2003 | Sagara | |
| 2002/0006664 A1 | 1/2002 | Sabatini | |
| 2002/0009807 A1 | 1/2002 | Kam et al. | |
| 2002/0013283 A1 | 1/2002 | Tomalia et al. | |
| 2002/0052443 A1 | 5/2002 | Greenwald et al. | |
| 2002/0146825 A1 | 10/2002 | Uhler | |
| 2003/0027784 A1 | 2/2003 | Kissel et al. | |
| 2003/0099927 A1 | 5/2003 | Wang et al. | |
| 2003/0215395 A1 | 11/2003 | Yu et al. | |
| 2004/0048260 A1 | 3/2004 | Chang et al. | |
| 2004/0120979 A1 | 6/2004 | Roessler et al. | |
| 2004/0138154 A1 | 7/2004 | Yu et al. | |
| 2005/0176132 A1 | 8/2005 | Tanaka et al. | |

FOREIGN PATENT DOCUMENTS

| | | |
|---|---|---|
| EP | 1 398 042 | 3/2004 |
| WO | WO 97/45069 | 12/1997 |
| WO | WO 01/20015 | 3/2001 |
| WO | WO 02/22174 | 3/2002 |
| WO | WO 02/42447 | 5/2002 |
| WO | WO 02/077264 | 10/2002 |
| WO | WO 02/100435 | 12/2002 |

OTHER PUBLICATIONS

Kircheis et al., Gene Therapy, 1997, 4: 409-418.*
Berle, et al. "Characterization of Surfactant Coatings in Capillary Electrophoresis by Atomic Force Microscopy," *Anal. Cham.*, vol. 73, pp. 4558-4565, 2001.
Chu, et al. "Industrial Choices for Protein Production by Large-Scale Cell Culture," *Current Opinion in Biotechnology*, vol. 12, pp. 180-187, 2001.
Connolly, et al. "Fast Ion Chromatography of Common Inorganic Anions on a Short ODS Column Permanently Coated with Didodecyldimethylammonium Bromide," *Journal of Chromatography A*, vol. 953, pp. 299-303, 2002.
Honma, et al. "Atelocollagen-Based Gene Transfer in Cells Allows High-Throughput Screening of Gene Functions," *Biochemical and Biophysical Research Communications*, vol. 289, pp. 1075-1081, 2001.
Kam, et al. "Cell Adhesion to Protein-Micropatterned-Supported Lipid Bilayer Membranes," *Biomed. Mater. Res.*, vol. 55, pp. 487-495, 2001.
Luo, et al. "Enhancement of Transfection by Physical Concentration of DNA at the Cell Surface," *Nature Biotechnology*, vol. 18, pp. 893-895, Aug. 2000.
Manuel, et al. "Transfection by Polyethyleneimine-Coated Microspheres," *Journal of Drug Targeting*, vol. 9, No. 1, pp. 15-22, 2001.
Melanson, et al. "Double-Chained Surfactants for Semipermanent Wall Coatings in Capillary Electrophoresis," *Analytical Chemistry*, vol. 72, No. 17, pp. 4110-4114, Sep. 2000.
Merdan, et al. Prospects for Cationic Polymers in Gene Oligonucleotide Therapy Against Cancer, *Advanced Drug Delivery Reviews*, vol. 54, pp. 715-758, 2002.
Ochiya, et al. "New Delivery System for Plasmid DNA in Vivo Using Atelocollagen as a Carrier Material: The Minipellet," *Nature Medicine*, vol. 5, No. 6, pp. 707-710, Jun. 1999.
Segura, et al. "Surface-Tethered DNA Complexes for Enhanced Gene Delivery," *Bioconjugate Chem.*, vol. 13, pp. 621-629, 2002.
Shea, et al. "DNA Delivery from Polymer Matrices for Tissue Engineering," *Nature Biotechnology*, vol. 17, pp. 551-554, Jun. 1999.
Clark, et al. "Cationic Lipid-Mediated Gene Transfer: Current Concepts," *Curr. Opin. Mol. Ther.*, vol. 1, No. 2, pp. 158-176, Apr. 1999 (abstract only).
Lynn, et al. "Accelerated Discovery of Synthetic Transfection Vectors: Parallel Synthesis and Screening of a Degradable Polymer Library," *Journal of the American Chemical Society*, vol. 123, pp. 8155-8156, 2001.
Gosselin, et al. "Efficient Gene Transfer Using Reversibly Cross-Linked Low Molecular Weight Polyethylenimine," *Bioconjugate Chem.* vol. 12, pp. 989-994, 2001.
Boussif, et al. "A Versatile Vector for Gene and Oligonucleotide Transfer into Cells in Culture and in Vivo: Polyethyenimine," *Proc Natl Acad Sci* USA, vol. 92, pp. 7297-7301, Aug. 1995.
Zheng, et al. Biotechnol Prog, 2000, 16: 254-257.
Bielinska, et al. Biomaterials, 2000, 21: 877-887.

(Continued)

*Primary Examiner* — Ileana Popa

(74) *Attorney, Agent, or Firm* — Knobbe, Martens, Olson & Bear, LLP

(57) ABSTRACT

The present invention is related to a method for introducing biomolecules, such as nucleic acids, into cells by culturing cells on a solid surface which is coated with a transfection reagents and biomolecules.

38 Claims, 35 Drawing Sheets

OTHER PUBLICATIONS

Dwyer, et al. Neurochem Res, 1998, 23: 1107-1116.

Ziauddin, et al. Nature, 2001, 411: 107-110.

Pollard, et al. J. Biol Chem, 1998, 278: 7507-7511.

Fenske, et al. "Cationic Poly(ethyleneglycol) Lipids Incorporated into Pre-Formed Vesicles Enhance Binding and Uptake to BHK Cells," *Biochimica et Biophysica Acta*, No. 1512, pp. 259-272, 2001.

Hong, et al. "Stabilization of Cationic Liposome-Plasmid DNA Complexes by Polyamines and Poly(ethylene glycol)-Phospholipid Conjugates foe Efficient in Vivo Gene Delivery," *F.E.B.S. Letters*, No. 400, pp. 233-237, 1997.

Chang, et al. "Surfection: A New Platform for Transfected Cell Arrays," *Nucleic Acids Research*, vol. 32, No. 3, pp. 1-6, Feb. 18, 2004.

Supplementary European Search Report dated Feb. 21, 2006.

International Search Report mailed May 27, 2004.

Petersen, et al. "Poly(ethylenimine-*co*-L-lactamide-*co*-succinamide): A Biodegradable Polyethylenimine Derivative with an Advantageous pH-Dependent Hydrolytic Degradation for Gene Delivery," *Bioconjugate Chem*, vol. 13, pp. 812-821, 2002.

Lynn, et al. "Degradable Poly(β-amino esters): Synthesis, Characterization, and Self-Assembly with Plasmid DNA," *J. Am. Chem. Soc.*, vol. 122, pp. 10761-10768, 2000.

Bettinger, et al. "Peptide-Mediated RNA Delivery: A Novel Approach for Enhanced Transfection of Primary and Post-Mitotic Cells," *Nucleic Acids Research*, vol. 29, No. 18, pp. 3882-3891, 2001.

Petersen, et al. "Star-Shaped Poly(ethylene glycol)-*block*-polyethylenimine Copolymers Enhance DNA Condensation of Low Molecular Weight Polyethylenimines," *Biomacromolecules*, vol. 3, No. 5, pp. 926-936, 2002.

Bieber, et al. "Preparation of a Low Molecular Weight Polyethylenimine for Efficient Cell Transfection," *BioTechniques*, vol. 30, No. 1, pp. 74-81, 2001.

Rudolph, et al. "Oligomers of the Arginine-rich Motif of the HIV-1 TAT Protein are Capable of Transferring Plasmid DNA into Cells," *The Journal of Biological Chemistry*, vol. 278, No. 13, pp. 11411-11418, Mar. 2003.

Bledi, et al. "Culturing Neuronal Cells on Surfaces Coated by a Novel Polyethyleneimine-based Polymer," *Brain Research Protocols*, vol. 5, pp. 282-289, 2000.

de Semir, et al. "Non-viral Vector-mediated Uptake, Distribution, and Stability of Chimeraplasts in Human Airway Epithelial Cells," *The Journal of Gene Medicine*, vol. 4, pp. 308-322, 2002.

\* cited by examiner

NDT-CP-1  lipofectamine 2000

NDT-CP-1　　　　　　　lipofectamine 2000

NDT-CP-1　　　　　　lipofectamine 2000

NDT-CP-1 lipofectamine 2000

Before incubation	After incubation at 37· for 9 days

FIGURE 35

| | Polyaminine | Linker |
|---|---|---|
| NDT-CP-B-1 | Branch PEI 600 | 1,6-Hexanediol diacrylate (Aldrich, 90%) $$H_2C=HC-\overset{O}{\underset{\|}{C}}-O-CH_2(CH_2)_4CH_2-O-\overset{O}{\underset{\|}{C}}-CH=CH_2$$ |
| NDT-CP-1 | Branch PEI 600 | Glycerol diglycidyl ether. (Aldrich) |
| NDT-LP-1 and NDT-LP-2 | Cholesteryl-conjugated PEI | |

NDT-LP-1: Molecular weight of PEI oligomer is 1800, the weight percentage of cholesteryl is about 25%

NDT-LP-2: Molecular weight of PEI is 25000, the weight percentage of cholesteryl is about 3%

SEQUENCE LISTING

<160> NUMBER OF SEQ ID NOS: 2

<210> SEQ ID NO 1
<211> LENGTH: 18

```
<212> TYPE: RNA
<213> ORGANISM: Artificial Sequence
<220> FEATURE:
<223> OTHER INFORMATION: Chemically synthesized oligonucleotide

<400> SEQUENCE: 1
ccucuuaccu caguuaca                                                 18

<210> SEQ ID NO 2
<211> LENGTH: 28
<212> TYPE: PRT
<213> ORGANISM: Artificial Sequence
<220> FEATURE:
<223> OTHER INFORMATION: Chemically synthesized peptide corresponding to
      viral envelope protein VSVG

<400> SEQUENCE: 2

Arg Arg Arg Gln Gly Thr Trp Leu Asn Pro Gly Phe Pro Pro Gln Ser
1               5                   10                  15

Cys Gly Tyr Ala Thr Val Thr Asp Ala Arg Arg Arg
            20                  25
```

US 8,192,989 B2

SOLID SURFACE FOR BIOMOLECULE DELIVERY AND HIGH-THROUGHPUT ASSAY

RELATED APPLICATIONS

This application is a continuation of U.S. application Ser. No. 10/341,059 filed Jan. 13, 2003 which is incorporated herein by reference.

FIELD OF THE INVENTION

The present invention is related to a method for introducing biomolecules, such as nucleic acids, into cells by culturing cells on a solid surface which is coated with a transfection reagents and biomolecules for routine transfection assays and high-throughput transfection assays. The present invention is also related to method of use and method of making the transfectable surface for such assays.

BACKGROUND OF THE INVENTION

Gene transfection methods can be used to introduce nucleic acids into cells and are useful in studying gene regulation and function. High throughput assays that can be used to screen large sets of DNAs to identify those encoding products with properties of interest are particularly useful. Gene transfection is the delivery and introduction of biologically functional nucleic acids into a cell, such as a eukaryotic cell, in such a way that the nucleic acid retains its function within the cell. Gene transfection is widely applied in studies related to gene regulation, gene function, molecular therapy, signal transduction, drug screening, and gene therapy studies. As the cloning and cataloging of genes from higher organisms continues, researchers seek to discover the function of the genes and to identify gene products with desired properties. This growing collection of gene sequences requires the development of systematic and high-throughput approaches to characterizing gene products and analyzing gene function, as well as other areas of research in cell and molecular biology.

Both viral and non-viral gene carriers have been used in gene delivery. Viral vectors have been shown to have higher transfection efficiency than non-viral carriers, but the safety of viral vectors hampers its applicability (Verma I. M and Somia N. *Nature* 389 (1997), pp. 239-242; Marhsall E. *Science* 286 (2000), pp. 2244-2245). Although non-viral transfection systems have not exhibited the efficiency of viral vectors, they have received significant attention, because of their theoretical safety when compared to viral vectors. In addition, viral vector preparation is a complicated and expensive process, which limits the application of viral vectors in vitro. The preparation of non-viral carriers is simpler and more cost effective in comparison to preparation of viral carriers, making synthetic gene carriers desirable as transfection reagents in in vitro studies.

Most non-viral vectors mimic important features of viral cell entry in order to overcome cellular barriers, which are meant to prevent infiltration by foreign genetic material. Non-viral gene vectors, based on a gene carrier backbone, can be classified as a) lipoplexes, b) polyplexes, and c) lipopolyplexes. Lipoplexes are assemblies of nucleic acids with a lipidic component, which is usually cationic. Gene transfer by lipoplexes is called lipofection. Polyplexes are complexes of nucleic acids with cationic polymer. Lipopolyplexes comprise both a lipid and a polymer component. Often such DNA complexes are further modified to contain a cell targeting or an intracellular targeting moiety and/or a membrane-destabilizing component, for example, a viral protein or peptide or a membrane-disruptive synthetic peptide. Recently, bacteria and phages have also been described as shuttles for the transfer of nucleic acids into cells.

Most non-viral transfection reagents are synthetic cationic molecules and have been reported to "coat" the nucleic acid by interaction of the cationic sites on the cation and anionic sites on the nucleic acid. The positively-charged DNA-cationic molecule complex interacts with the negatively charged cell membrane to facilitate the passage of the DNA through the cell membrane by non-specific endocytosis. (Schofield, Brit. Microencapsulated. Bull, 51(1):56-71 (1995)). In most conventional gene transfection protocols, the cells are seeded on cell culture devices 16 to 24 hours before transfection. The transfection reagent (such as a cationic polymer carrier) and DNA were usually prepared in separate tubes, and each respective solution was diluted in medium (containing no fetal bovine serum or antibiotics). The solutions were then mixed by carefully and slowing adding one solution to the other while continuously vortexing the mixture. The mixture was incubated at room temperature for 15-45 minutes to allow the transfection reagent-DNA complexes formation to remove the residues of serum and antibiotics. Prior to transfection, the cell culture medium was removed and the cells were washed with buffer. The solution containing DNA-transfection reagent complexes was added to the cells, and the cells were incubated for about 3-4 hours. The medium containing transfection reagent would then be replaced with fresh medium. The cells would finally be analyzed at one or more specific time point(s). This is obviously a time consuming procedure, particularly when the number of samples to be transfected is very large.

Several major problems exist in conventional transfection procedures. First, conventional procedures are time-consuming, particularly when there are many cell or gene samples to be used in transfection experiments. Also, the results derived from common transfection procedures are difficult to reproduce, due to the number of steps required. For instance, in producing the DNA-transfection reagent complex formation of the complex is influenced by concentration and volume of nucleic acid and reagents, pH, temperature, type of buffer(s) used, length and speed of vortexing, incubation time, and other factors. Although the same reagents and procedure may be followed, different results may be obtained. Results derived from multi-step procedures are often influenced by human or mechanical error or other variations at each step. In addition, refreshing the cell culture medium following transfection disturbs the cells and may cause them to detach from the surface on which they are cultured, thus leading to variation and unpredictability in the final results. Due to all the factors noted, conventional transfection methods require a highly skilled individual to perform the transfection experiment or assay.

Researchers require an easier and more cost effective method of transfecting cells, and a high-throughput method of transfecting cells is needed in order to transfect large sample numbers efficiently.

SUMMARY OF THE INVENTION

A method for introducing biomolecules into eukaryotic cells is provided comprising (a) coating a solid surface with a biomolecule delivery reagent, (b) adding the biomolecules to be introduced into the eukaryotic cells onto the solid surface, (c) seeding cells on the solid surface at a sufficient density and under appropriate conditions for introduction of the biomolecules into the eukaryotic cells. According to embodiments of the invention the surface may be selected from the group consisting of flasks, dishes, multi-well plates, glass slides, and implanted devices. The biomolecule delivery reagent or transfection reagent may be selected from the group consisting of polymers, lipids, lipid-polymers and/or their combinations and/or their derivatives containing a cell-targeting or an intracellular targeting moiety and/or a membrane-destabilizing component and one or more delivery enhancers.

According to embodiments of the invention the biomolecule delivery reagent can be affixed on the surface by evenly spreading the reagent on the surface or spotting said biomolecule delivery reagent in discrete areas of the surface. The solid surface coated with a biomolecule delivery reagent may further comprise a matrix reagent selected from the group consisting of proteins, peptides, polysaccharides, and polymers. The protein may be selected from gelatin, bovine serum albumin, and extracellular matrix components such as, but not limited to collagen, laminin, and fibronectin. The polymer may be selected from hydrogels, biodegradable polymers, and biocompatible materials.

According to embodiments of the invention a solid surface is coated with a biomolecule delivery reagent which further comprises a cell culture reagent selected from the group consisting of cytoreductive reagents, cell binding/attaching reagents, cell growing reagents, cell stimulating reagents, and cell inhibiting reagents.

Biomolecules may be selected from nucleotides, proteins, peptides, sugars, polysaccharides, and organic compounds. Preferably the biomolecules are selected from DNA, RNA, and DNA/RNA hybrids. The nucleotides may be circular (plasmid), linear, or single strand oligodeoxynucleotide. RNA may be single stranded (ribozyme) or double stranded (siRNA).

Solid surfaces used according to methods described herein may be selected from, but not limited to, a slide or a multi-well plate.

Eukaryotic cells used according to embodiments of the invention may be, but are not limited to, mammalian cells. The mammalian cells may be dividing cells or non-dividing cells. The mammalian cells may be transformed cells or primary cells. The mammalian cells may be somatic cells or stem cells. The eukaryotic cells may be plant, yeast, or insect cells.

A method of high throughput drug screening assay is provided comprising (a) affixing a delivery reagent to a solid surface, (b) affixing biomolecules to be introduced into eukaryotic cells to said delivery reagent, (c) seeding cells on the surface bearing delivery reagent and biomolecules with sufficient density and under appropriate conditions for introduction of the biomolecules into the eukaryotic cells, and (d) detecting eukaryotic cells into which the biomolecule has been delivered.

The biomolecules may be selected from, but not limited to, nucleotides, proteins, peptides, sugars, polysaccharides, and organic compounds. The nucleotides may be selected from, but not limited to, DNA, RNA, and DNA/RNA hybrid. The DNA may be circular (plasmid), linear, or single stranded oligodeoxynucleotide (ODN). The RNA may be single stranded (ribozyme) or double stranded (siRNA).

The eukaryotic cells are preferably mammalian cells. The mammalian cells may be dividing cells or non-dividing cells and the cells may be transformed cells or primary cells. The mammalian cells may be somatic cells or stem cells. The eukaryotic cells may be selected from, but not limited to plant, bacterial, and insect cells. Detecting cells into which the biomolecule has been delivered may be performed by detecting the biomolecule itself, its product, its target molecule, the products catalyzed or products regulated by the biomolecule.

BRIEF DESCRIPTION OF THE DRAWINGS

In FIG. 26A, Tat was coated in solid surface with gelatin matrix. FIG. 26B shows the non-Tat control. About 60-80% cells showed FITC signal in the Tat-coated group. This indicates that not only nucleic acid, but also peptides, can be delivered into cells according to embodiments of the present invention.

FIG. 35 is a table illustrating the structures of NDT synthesized polymers and lipid-polymers.

DETAILED DESCRIPTION OF THE PREFERRED EMBODIMENT

Figure 1:
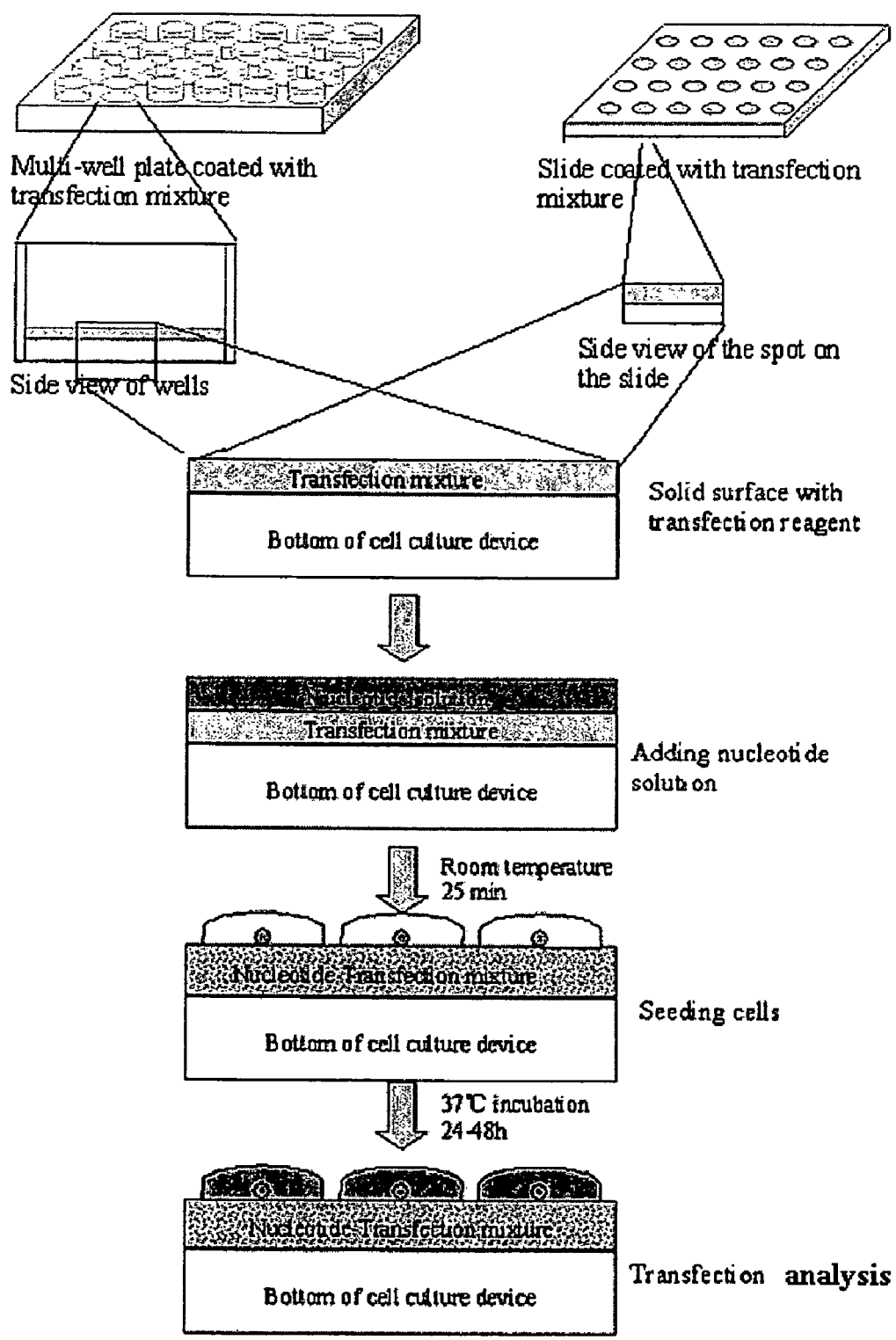
FIG. 1 is a schematic of a transfection assay using transfectable cell culture devices or slides.
Figure 2:
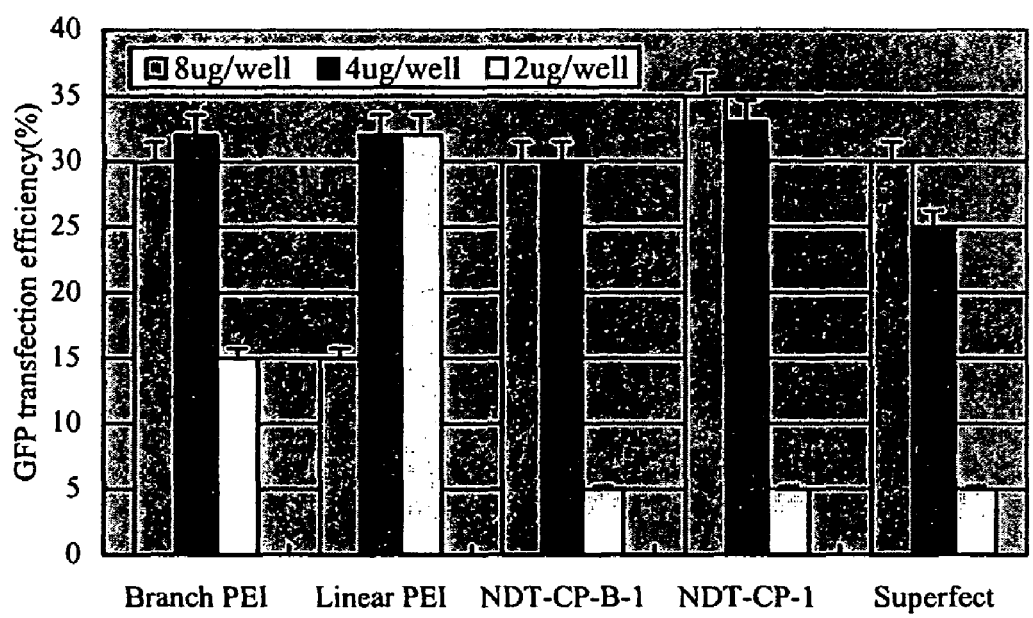
FIG. 2 illustrates the effect of using a transfectable surface coated with various cationic polymers-gelatin transfection mixture on GFP reporter gene transfection in 923 cells in 96-well plate cell culture device system. The amount of Linear PEI, NDT-CP-B-1 and NDT-CP-1 were showed in the figure. The amounts of Superfect were 15, 7.5 and 3.75 µg/well, respectively. The ranges of GFP gene transfection efficiency are approximately 30-35%, and NDT-CP-1 showed the highest efficiency.
Figure 3:
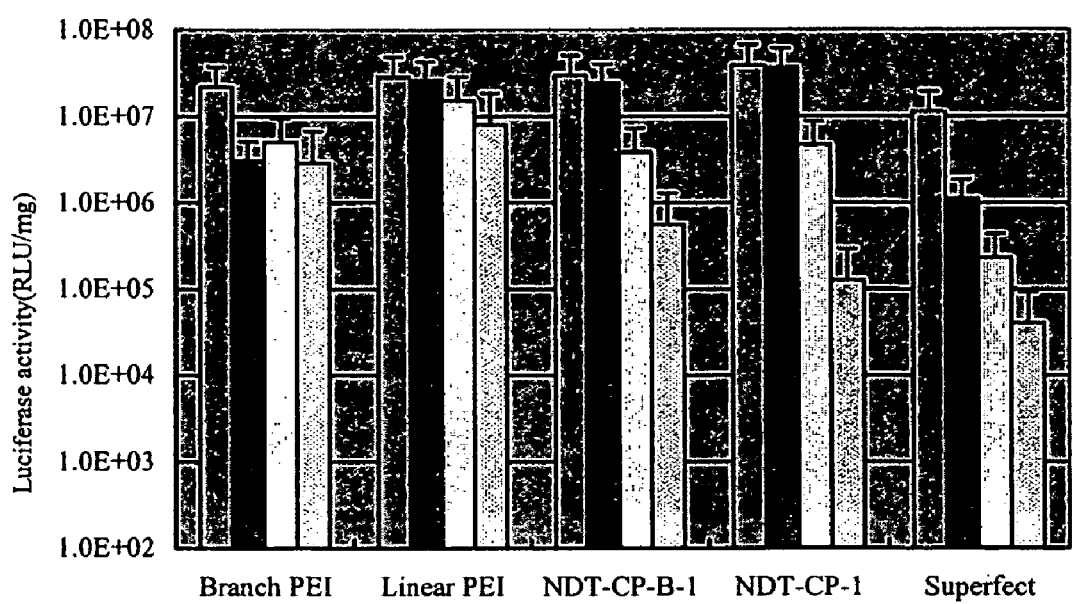
FIG. 3 illustrates the effect of using a transfectable surface coated with various cationic polymers-gelatin transfection mixture on luciferase reporter gene transfection in 923 cells in a 96-well plate cell culture device system. The amounts of Linear PEI, NDT-CP-B-1 and NDT-CP-1 were 8, 4, 2, and 1 µg/well, respectively. The amounts of Superfect were 15, 7.5 and 3.75 µg/well. The luciferase activities of all samples were higher than $5 \times 10^7$ RLU/mg protein.
Figure 4:
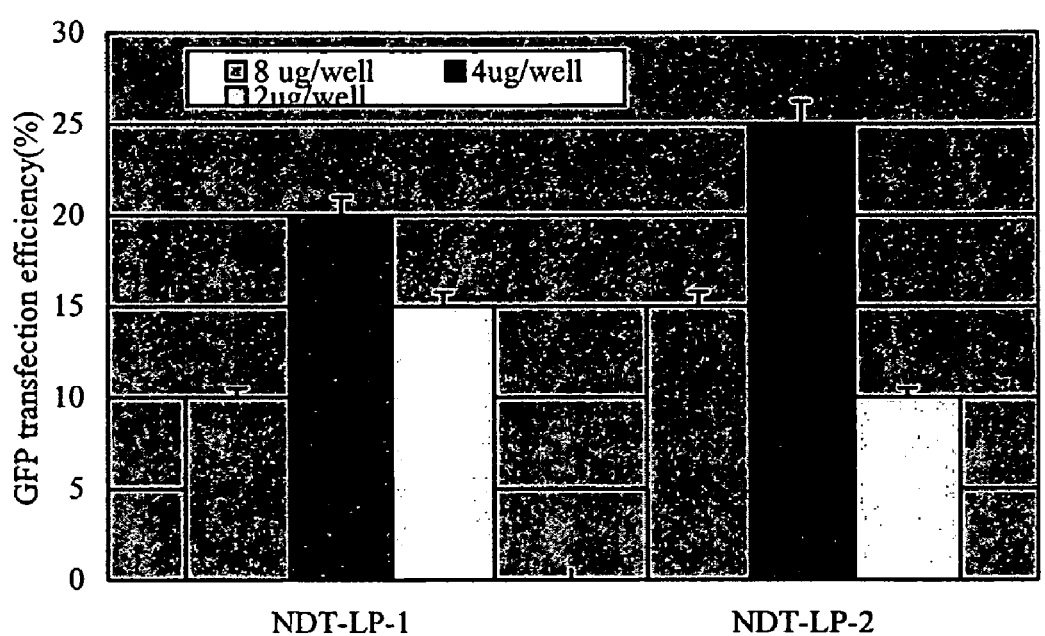
FIG. 4 illustrates the effect of using a transfectable surface coated with various cationic lipid-polymer-gelatin transfection mixture on GFP reporter gene transfection in 923 cells in a 96-well plate cell culture device system. The amount of lipid-polymer was shown as 8, 4, and 2 µg/well. The GFP transfection efficiency could reach 20-25% in tested lipid-polymer transfection reagents.
Figure 5:
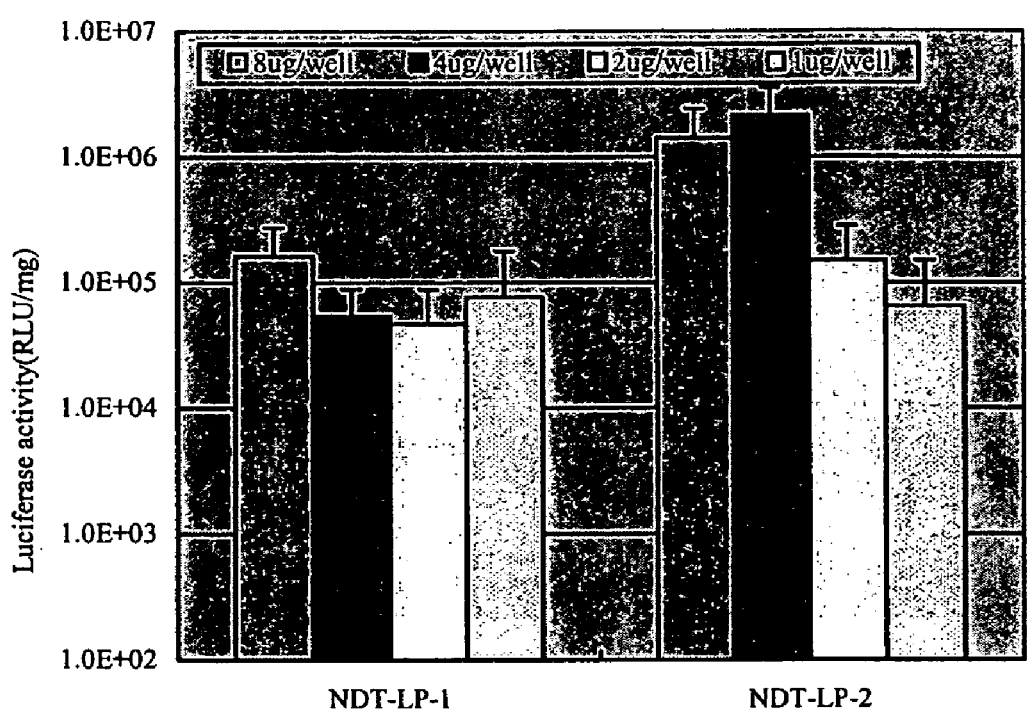
FIG. 5 illustrates the effect of using a transfectable surface coated with various cationic lipid-polymer-gelatin transfection mixture on luciferase reporter gene transfection in 923 cells in a 96-well plate cell culture device system. The luciferase activity of NDT-LP-2 could reach higher than $10^6$ RLU/mg protein in a lipid-polymers-gelatin transfection mixture system.
Figure 6:
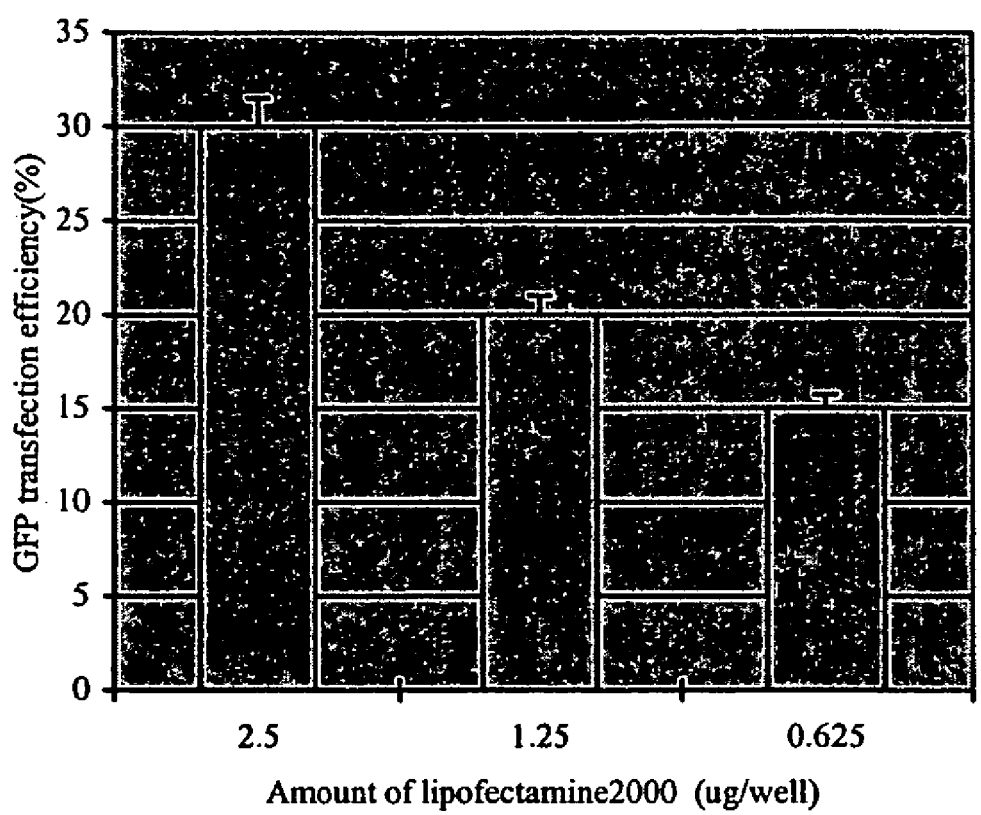
FIG. 6 illustrates the effect of using a transfectable surface coated with cationic lipid-gelatin transfection mixture on GFP reporter gene transfection in 923 cells in a 96-well plate cell culture device system. The transfection efficiency mediated by lipofectamine2000-gelatin transfection mixture in a 96-well-plate system could reach up to 30%.
Figure 7:
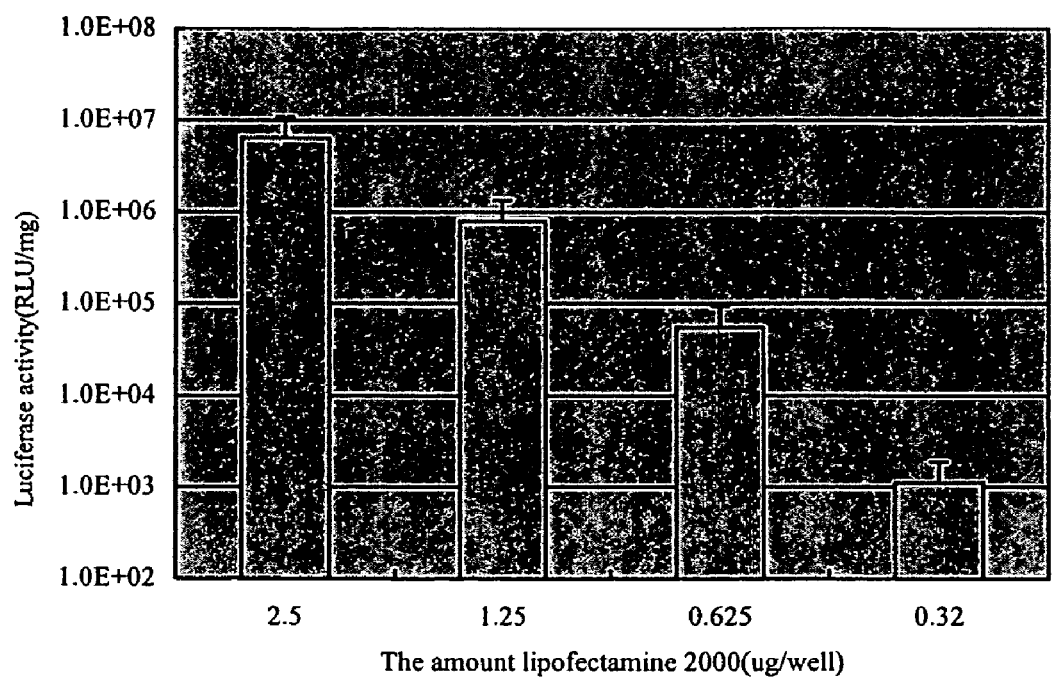
FIG. 7 illustrates the effect of using a transfectable surface coated with cationic lipid-gelatin transfection mixture on luciferase reporter gene transfection in 923 cells in a 96-well plate cell culture device system. The luciferase activity of lipofectamine 2000 could reach up to near $10^7$ RLU/mg proteins in lipid-gelatin transfection mixture system.
Figure 8:
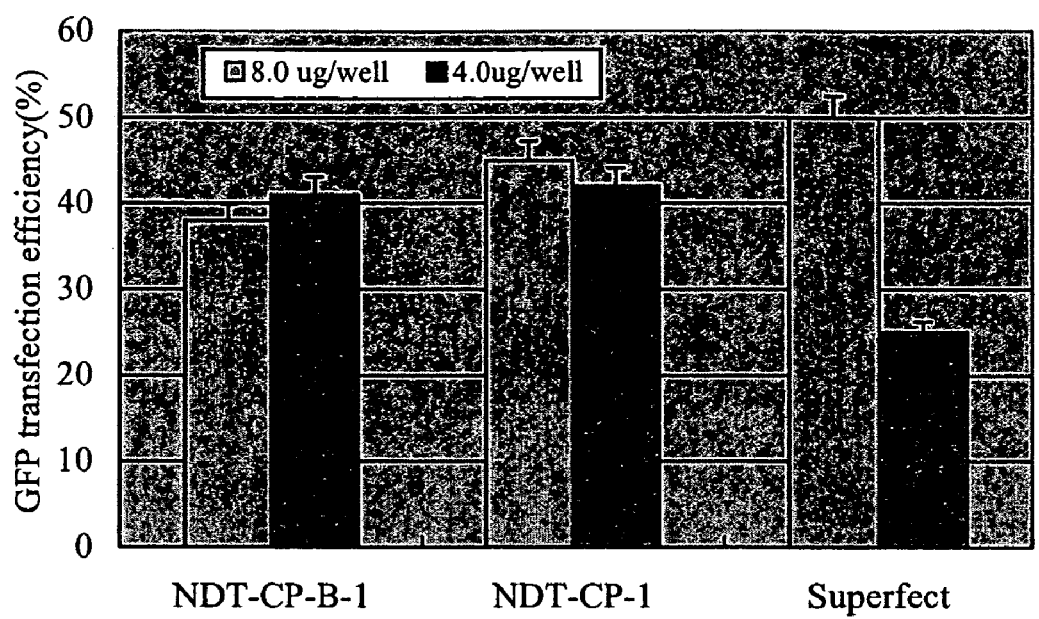
FIG. 8 illustrates the effect of using a transfectable surface coated with cationic polymer-laminin transfection mixture on GFP reporter gene transfection in 923 cells in a 96-well plate cell culture device system. The amounts of NDT-CP-1 and NDT-CP-B-1 are shown in the figure. The amounts of Superfect were 15 and 7.5 µg/well respectively. The GFP transfection efficiency mediated by cationic polymer-laminin system could reach up to 50%.
Figure 9:
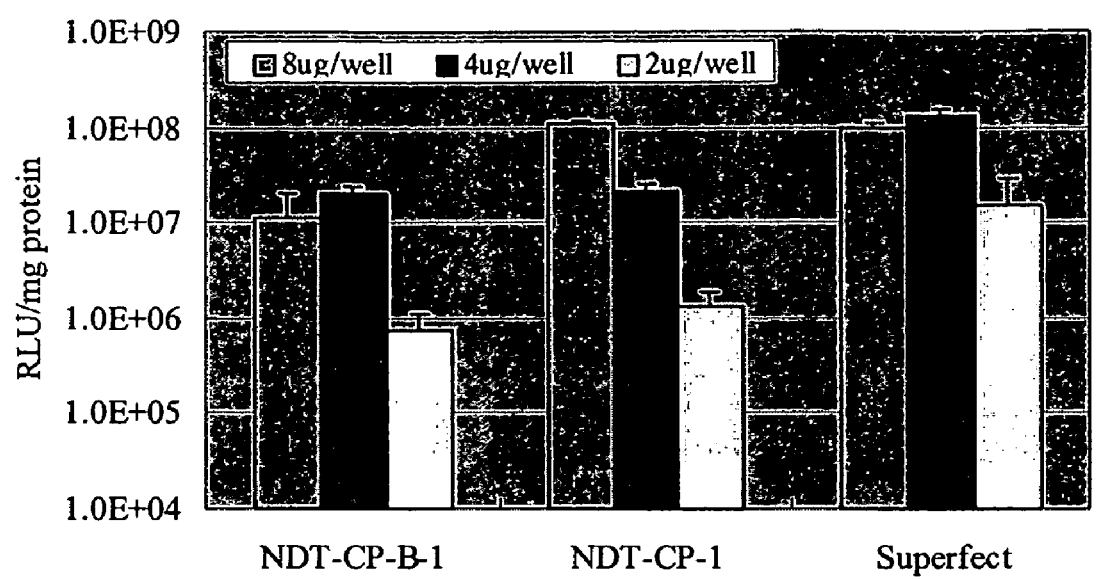
FIG. 9 illustrates the effect of using a transfectable surface coated with cationic polymer-laminin transfection mixture on luciferase reporter gene transfection in 923 cells in a 96-well plate cell culture device system. The amount of NDT-CP-1 and NDT-CP-B-1 are shown in the figure. The amounts of Superfect were 15 and 7.5 and 3.75 µg/well respectively. The luciferase activity of cationic polymer-laminin system could reach up to $10^8$ RLU/mg protein.
Figure 10:
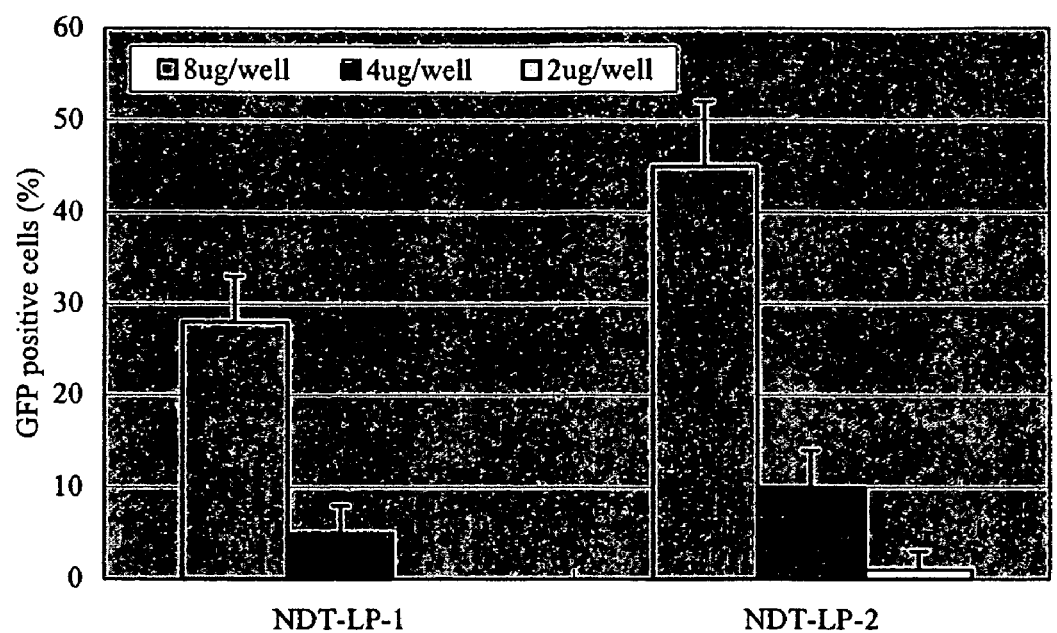
FIG. 10 illustrates the effect of using a transfectable surface coated with cationic lipid-polymer-laminin transfection mixture on GFP reporter gene transfection in 923 cells in a 96-well plate cell culture device system. The amount of lipid-polymer was shown as 8, 4, and 2 µg/well. The GFP transfection efficiency mediated by lipid-polymer-laminin transfection mixture system could reach up to 45%.
Figure 11:
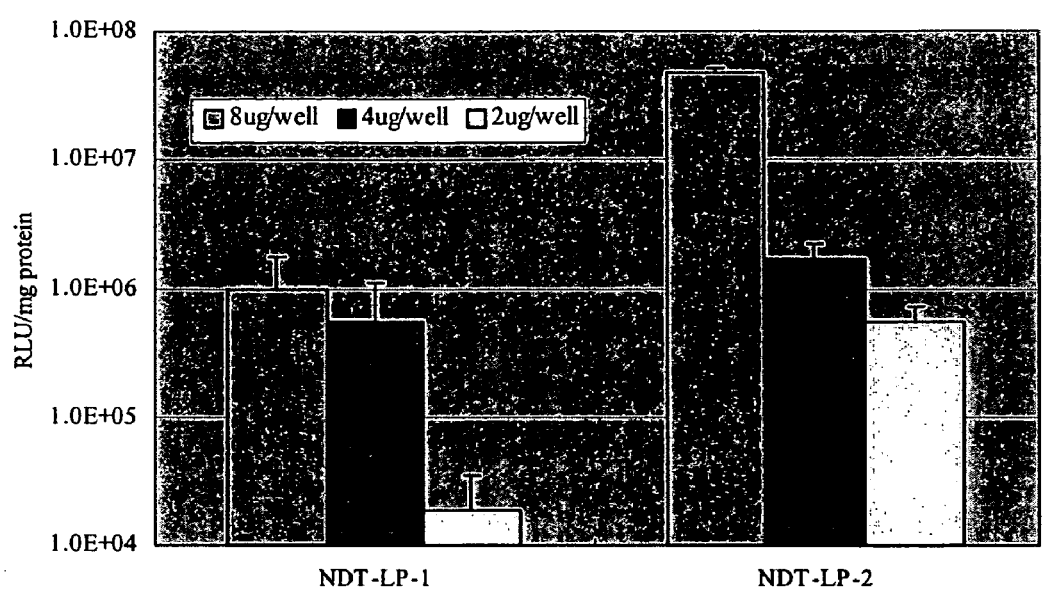
FIG. 11 illustrates the effect of using a transfectable surface coated with cationic lipid-polymer-laminin transfection mixture on luciferase reporter gene transfection in 923 cells in a 96-well plate cell culture device system. The amount of lipid-polymer is shown in the figure. The luciferase activity of lipid polymer-laminin transfection mixture system could reach up to $8 \times 10^7$ RLU/mg of protein.
Figure 12:
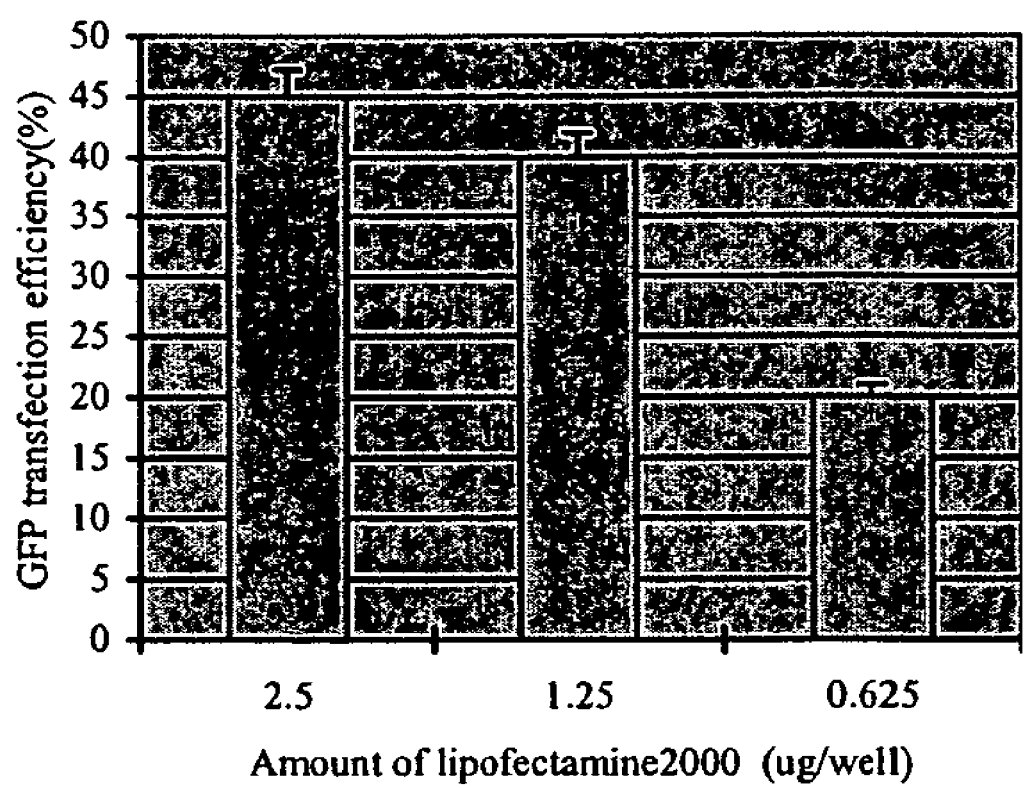
FIG. 12 illustrates the effect of using a transfectable surface coated with cationic lipid-laminin transfection mixture on GFP reporter gene transfection in 923 cells in a 96-well plate cell culture device system. The transfection efficiency mediated by lipofectamine-laminin transfection mixture system could reach up to 45%.
Figure 13:
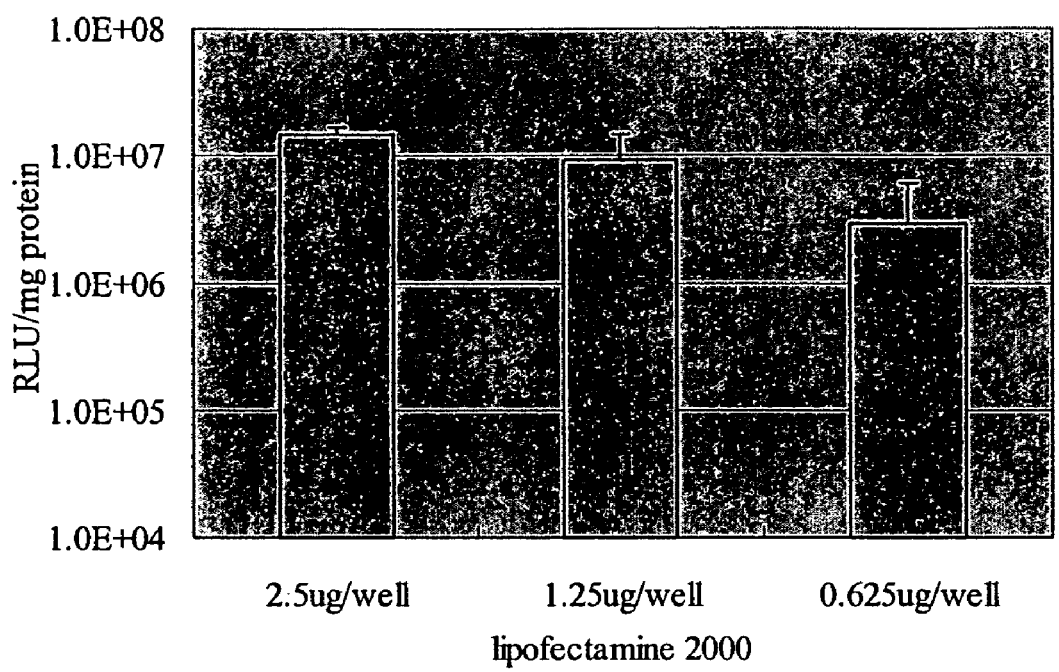
FIG. 13 illustrates the effect of using a transfectable surface coated with cationic lipid-laminin transfection mixture on luciferase reporter gene transfection in 923 cells in a 96-well plate cell culture device system. The luciferase activity of lipofectamine 2000-laminin transfection mixture system could reach up to $1.5 \times 10^7$ RLU/mg protein.

A novel transfection device and method are described herein which is simple, convenient, and efficient compared to conventional transfection assays. A transfection device is made according to methods described herein by affixing a transfection reagent on the solid surface of a cell culture device. By using this device, researchers need only add a nucleic acid or other biomolecule carrier system to the surface of the cell culture device. There is no need to pre-mix the DNA or biomolecule with a transfection reagent. This removes a key timing-consuming step, which is required by conventional transfection procedures. Scientists only require approximately 40 minutes to complete the entire transfection process for 10 samples, compared to 2 to 5 hours or more required by current methods. This is particularly favorable for high throughput transfection assays, in which hundreds of samples will be tested at a time.

As compared to conventional transfection, there are several advantages to the new method described herein. It provides a transfection device that is very easy to store, and it provides a simple method for biomolecule delivery or gene transfection in which no biomaterial/transfection reagent mixing step is required. The transfection procedure described herein can be finished in a short period of time, for instance approximately 40 minutes, and it provides a high throughput method for transfection or drug delivery in which large numbers of samples may be transfected at a time.

A novel method and device for gene delivery are described herein, which overcome the common problems encountered in conventional transfection assays described above. Transfection reagents are simply coated onto the surface of a cell culture device, which can be easily commercialized and mass-produced. Customers, researchers for instance, need only add a biomolecule, such as a nucleic acid of interest, directly to the surface of a cell culture device in order to prepare the device prior to transfection. Cells are then seeded on the surface of the cell culture device and incubated, without changing the medium, and the cells are analyzed. Changing medium during transfection procedure is unnecessary. The methods described herein dramatically reduce the risk of error, by reducing the number of steps involved, thus increasing consistency and accuracy of the system.

According to the methods described herein, transfection reagents were affixed on the surface of a slide, multi-well plate, or other surface to form a transfection device. By using this device, people need only add DNA or other biomolecule to the surface and allow the transfection reagent to form a complex with the DNA or biomolecule. This reaction occurs in approximately 30 minutes, then cells are seeded on the surface and incubated in suitable condition for introduction of the biomolecule(s) into the cells.

Any suitable surface that can be used to affix the nucleic acid/biomolecule-containing mixture to its surface can be used. For example, the surface can be glass, plastics (such as polytetrafluoroethylene, polyvinylidenedifluoride, polystyrene, polycarbonate, polypropylene), silicon, metal, (such as gold), membranes (such as nitrocellulose, methylcellulose, PTFE or cellulose), paper, biomaterials (such as protein, gelatin, agar), tissues (such as skin, endothelial tissue, bone, cartilage), minerals (such as hydroxylapatite, graphite). According to preferred embodiments the surfaces may be slides (glass or poly-L-lysine coated slides) or wells of a multi-well plate.

For slides, such as a glass slide coated with poly-L-lysine (e.g., Sigma, Inc.), the transfection reagents are fixed on the surface and dried, and then a nucleic acid of interest or a nucleic acid to be introduced into cells, a protein, peptide, or small molecule drug is introduced. The slide is incubated at room temperature for 30 minutes to form biomolecule/transfection reagent complexes on the surface of the transfection device. The biomolecule/transfection reagent complexes create a medium for use in high throughput microarrays, which can be used to study hundreds to thousands of nucleic acids, proteins, peptides and other small molecular drugs at same time. In an alternative embodiment, the transfection reagents or drug delivery reagents can be affixed on the surface of the transfection device in discrete, defined regions to form a microarray of transfection reagents or drug delivery reagents. In this embodiment, molecules, such as nucleic acids, which are to be introduced into cells, are spread on the surface of the transfection device along with a transfection or delivery reagent. This method can be used in screening transfection reagents or other delivery reagents from thousands of compounds. The results of such a screening method can be examined through computer analysis.

In another embodiment of the invention one of more well of a multi-well plate may be coated with a transfection or drug delivery reagent. Plates commonly used in transfection and drug screening are 96-well and 384-well plates. The transfection or biomolecule delivery reagent can be evenly applied to the bottom of plate. Hundreds of nucleic acids, proteins, peptides or other biomolecules are then added into the well(s) by, for instance, a multichannel pipette or automated machine. Results of transfection are then determined by using a microplate reader. This is a very convenient method of analyzing the transfected cells, because microplate readers are commonly used in most biomedical laboratories. The multi-well plate coated with transfection or biomolecule delivery reagent can be widely used in most laboratories to study gene regulation, gene function, molecular therapy, and signal transduction, as well as drug screening. Also, if different kinds of transfection reagents are coated on the different wells of multi-well plates, the plates can be used to screen many transfection or delivery reagents relatively efficiently. Recently, 1,536 and 3,456 well plates have been developed, which may also be used according to the methods described herein.

The transfection reagent or delivery reagent are preferably cationic compounds which can introduce biomolecules, such as nucleic acids, proteins, peptides, sugars, polysaccharides, organic compounds, and other biomolecules into cells. Preferred embodiments use cationic oligomers, such as low molecular weight polyethyleneimine (PEI), low molecular weight poly(L-lysine) (PLL), low molecular weight chitosan, or low molecular weight dendrimers. According to their modular composition, reagents can be classified as: lipids, polymers, lipid-polymers and/or their combinations and/or their derivatives, which contain a cell-targeting or an intracellular-targeting moiety and/or a membrane-destabilizing component, as well as delivery enhancers.

According to an one embodiment, the delivery reagent can be mixed with a matrix, such as proteins, peptides, polysaccharides, or other polymers. The protein can be gelatin, collagen, bovine serum albumin or any other protein that can be used in affixing proteins to a surface. The polymers can be hydrogels, copolymers, non-degradable or biodegradable polymers and biocompatible materials. The polysaccharide can be any compound that can form a membrane and coat the delivery reagent, such chitosan. Other reagents, such as cytotoxicity reductive reagents, cell binding reagents, cell growing reagents, cell stimulating reagents or cell inhibiting reagents and the compounds for culturing specific cells, can be also affixed to the transfection device along with the transfection or delivery reagent.

According to another embodiment, a gelatin-transfection reagent mixture, comprising transfection reagent (e.g., lipid, polymer, lipid-polymer or membrane destabilizing peptide) and gelatin that is present in an appropriate solvent, such as water or double deionized water, may be affixed to the transfection device. In a further embodiment a cell culture reagent may also be present in the gelatin-transfection reagent mixture. The mixture is evenly spread onto a surface, such as a slide and multi-well plate, thus producing a transfection surface bearing the gelatin-transfection reagent mixture. In alternative embodiments, different transfection reagent-gelatin mixtures may also be spotted on discrete regions on the surface of the transfection device. The resulting product is allowed to dry completely under suitable conditions such that the gelatin-transfection reagent mixture is affixed at the site of application of the mixture. For example, the resulting product to can be dried at specific temperatures or humidity or in a vacuum-dessicator.

The concentration of transfection reagent present in the mixture depends on the transfection efficiency and cytotoxicity of the reagent. Typically there is a balance between transfection efficiency and cytotoxicity. At concentrations in which a transfection reagent is most efficient, while keeping cytotoxicity at an acceptable level, the concentration of transfection reagent is at the optimal level. The concentration of transfection reagent will generally be in the range of about 1.0 µg/ml to about 1000 µg/ml. In preferred embodiments, the concentration is from about 40 µg/ml to about 600 µg/ml. Similarly, the concentration of gelatin or another matrix depends on the experiment or assay to be performed, but the concentration will generally be in the range of 0.01% to 0.5% of the transfection reagent. According to embodiments shown in the examples the gelatin concentration is about 0.2% of the transfection reagent.

The molecules to be introduced into cells can be nucleic acids, proteins, peptides, peptide nucleic acid (PNA) and other biomolecules. The nucleic acid can be DNA, RNA and DNA/hybrid, etc. If the DNA used is present in a vector, the vector can be of any type, such as a plasmid (e.g. example, pCMV-GFP, pCMV-luc) or viral-based vector (e.g. pLXSN). The DNA can also be linear fragment with a promoter sequence (such CMV promoter) at the 5' end of the cDNA to be expressed and a poly A site at the 3' end. These gene expression elements allow the cDNA of interest to be transiently expressed in mammalian cells. If the DNA is the single strand oligodeoxynucleotide (ODN), for example antisense ODN, it can be introduced into cells to regulate target gene expression. In embodiments using RNA the nucleic acid may be single stranded (antisense RNA and ribozyme) or double stranded (RNA interference, SiRNA). In most cases, the RNA is modified in order to increase the stability of RNA and improve its function in down regulation of gene expression. In peptide nucleic acid (PNA), the nucleic acid backbone is replaced by peptide, which makes the molecule more stable. In particular embodiments the methods described herein can be used to introduce proteins, peptides and other molecules into cells for various purposes, for example molecular therapy, protein function studies, or molecule mechanism studies.

Under appropriate conditions, the biomolecules are added into the transfction device, which is coated with transfection or delivery reagent(s), to form biomolecule/delivery reagent complexes. The biomolecules are preferably dissolved in cell culture medium without fetal bovine serum and antibiotics, for example Dulbecco's Modified Eagles Medium (DMEM). If the transfection or delivery reagent is evenly affixed on the slide, the biomolecules can be spotted onto discrete locations on the slide. Alternatively, transfection or delivery reagents may be spotted on descrete locations on the slide, and the biomolecules can simply be added to cover the whole surface of the transfection device. If the transfection reagent or delivery reagent are affixed on the bottom of multi-well plates, the biomolecules are simply added into different wells by multi-channel pipette, automated device, or other method. The resulting product (transfection device coated with transfection or delivery reagent and biomolecules) is incubated for approximately 25 minutes room temperature to form the biomolecule/transfection reagent (or delivery reagent) complexes. In some cases, for example, the different kind of biomolecules are spotted on discrete location of slide, the DNA solution will be remove to produce a surface bearing biomolecules in complex with transfection reagent. In other case, the biomolecules solution can be kept on the surface. Sequently, cells in an appropriate medium and appropriate density are plated onto the surface. The resulting product (a surface bearing biomolecules and plated cells) is maintained under conditions that result in entry of the biomolecules into plated cells.

Suitable cells for use according to the methods described herein include prokaryotes, yeast, or higher eukaryotic cells, including plant and animal cells, especially mammalian cells. Eukaryotic cells, such as mammalian cells (e.g., human, monkey, canine, feline, bovine, or murine cells), bacterial, insect or plant cells, are plated onto the transfection device, which is coated with transfection or delivery reagent and biomolecules, in sufficient density and under appropriate conditions for introduction/entry of the biomolecule into the eukaryotic cells and either expression of the DNA or interaction of the biomolecule with cellular components. In particular embodiments the cells maybe selected from hematopoietic cells, neuronal cells, pancreatic cells, hepatic cells, chondrocytes, osteocytes, or myocytes. The cells can be fully differentiated cells or progenitor/stem cells.

In preferred embodiments, eukaryotic cells are grown in Dulbecco's Modified Eagles Medium (DMEM) containing 10% heat-inactivated fetal bovine serum (FBS) with L-glutamine and penicillin/streptomycin (pen/strep). It will be appreciated by those of skill in the art that certain cells should be cultured in a special medium, because some cells need special nutrition, such as growth factors and amino acids. The optimal density of cells depends on the cell types and the purpose of experiment. For example, a population of 70-80% confluent cells is preferred for gene transfection, but for oligonucleotide delivery the optimal condition is 30-50% confluent cells. In an example embodiment, if $5 \times 10^4$ 293 cells/well were seeded onto a 96 well plate, the cells would reach 90% confluency at 18-24 hours after cell seeding. For HeLa 705 cells, only $1 \times 10^4$ cells/well are needed to reach a similar confluent percentage in a 96 well plate.

After the cells are seeded on the surface containing biomolecules/delivery reagent, the cells are incubated under optimal conditions for the cell type (e.g. 37° C., 5-10% $CO_2$). The culture time is dependent on the purpose of experiment. Typically, the cells are incubated for 24 to 48 hours for cells to express the target gene in the case of gene transfection experiments. In the analysis of intracellular trafficking of biomolecules in cells, minutes to several hours of incubation may be required and the cells can be observed at defined time points.

The results of biomolecule delivery can be analyzed by different methods. In the case of gene transfection and antisense nucleic acid delivery, the target gene expression level can be detected by reporter genes, such as green fluorescent protein (GFP) gene, luciferase gene, or β-galactosidase gene expression. The signal of GFP can be directly observed under microscope, the activity of luciferase can be detected by a luminometer, and the blue product catalyzed by β-galactosidase can be observed under microscope or determined by a microplate reader. One of skill in the art is familiar with how these reporters function and how they may be introduced into a gene delivery system. The nucleic acid and its product, the protein, peptide, or other biomolecules delivered according to methods described herein and the target modulated by these biomolecules can be determined by various methods, such as detecting immunofluorescence or enzyme immunocytochemistry, autoradiography, or in situ hybridization. If immunofluorescence is used to detect expression of an encoded protein, a fluorescently labeled antibody that binds the target protein is used (e.g., added to the slide under conditions suitable for binding of the antibody to the protein). Cells containing the protein are then identified by detecting a fluorescent signal. If the delivered molecules can modulate gene expression, the target gene expression level can also be determined by methods such as autoradiography, in situ hybridization, and in situ PCR. However, the identification method depends on the properties of the delivered biomolecules, their expression product, the target modulated by it, and/or the final product resulting from delivery of the biomolecules.

EXAMPLES

Transfection Reagent

Branched $PEI_{25k}$ (polyethyleneimine of Mw 25 KDa) and Linear $PEI_{25K}$ (Mw 25 KDa) were purchased from Polysciences Inc. (Warrington, Pa., USA). Superfect™ (Qiagen, Valencia, Calif.) solutions were used as provided by the manufacturers. Transfection Reagent LipofectAMINE™ was purchased from Life Technologies (Gaithersburg, Md.)

and was used as provided by the manufacturers. NDT-CP-B-1 (degradable) and NDT-CP-1 (non-degradable) were polymeric transfection reagent synthesized by $PEI_{600}$ (Mw 600 Da) with different linkers. NDT-LP-1 was lipid-polymer containing polymer and lipid structure on the same molecule. The structures of NDT polymeric transfection reagents are shown in FIG. 35.

Transfectable Surface Preparation

Transfection Surface Prepared by Gelatin Based Transfection Mixture (0.2% Gelatin Preparation)

Gelatin powder Type B: 225 Bloom (Sigma, catalog #G-9391) was dissolved in sterile MilliQ water by gently swirling the solution for 15 minutes in a 60° C. water bath. The 0.2% gelatin solution was then cooled at room temperature, and while still warm (~37-40° C.), the solution was filtered through a 0.45 µm cellular acetate membrane (CA). One hundred ml of solution was prepared and stored in 50 ml aliquots of the filtered gelatin solution at 4° C.

Preparation of Transfection Mixture with Gelatin

All transfection reagents were diluted in the 0.2% gelatin solution. The concentration of linear $PEI_{25k}$ and specially synthesized polymer samples ranged from 320.0 µg/ml to 40.0 µg/ml, and the concentration of branched $PEI_{25k}$ ranged from 160.0 µg/ml to 20.0 µg/ml. The concentration of Superfect ranged from 600.0 to 75.0 µg/ml, and lipofectamine concentration ranged from 200.0 µg/ml to 25.0 µg/ml. The concentration of polymers and lipid-polymer synthesized (NDT) ranged from 320.0 µg/ml to 40.0 µg/ml.

Making Transfectable Surface with 96 Well Plate and Transfection Reagent-Gelatin Mixture The 25 µl transfection/gelatin solution was added to each well of a 96 well plate. The plate was shaken for several seconds to make sure the entire bottom surfaces were covered by transfection/gelatin solution. Then the plate was allowed to air-dry in a tissue culture hood for several hours (approximately 5-6 hours). The dried plate was stored at 4° C. and ready for use (FIG. 2-7).

Figure 20:
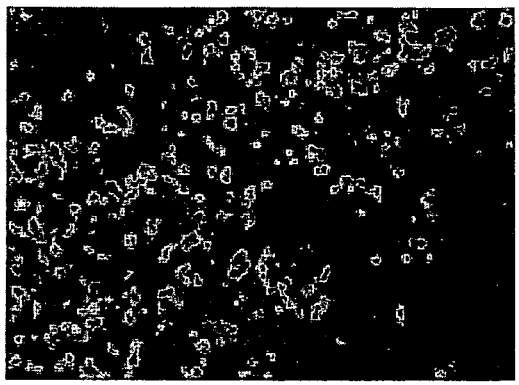
FIG. 20 illustrates a GFP reporter gene transfection assay in 923 cells with a transfectable glass slide system spotted with cationic polymer (NDT-CP-1)-gelatin or cationic lipid (lipofectamine2000)-gelatin transfection mixture. The transfectable slide was submerged in a GFP plasmid solution. Although the whole slide was covered with GFP plasmid solution, only the cells that are on the spot where the transfection mixtures were applied exhibited a GFP signal. This indicates that the transfection reagents were well affixed on the glass slide without diffusion. These results indicated that the current technology would be useful in transfection array applications, which could screen thousands of the target genes or gene medicine in cell based transfection assays for genomic function studies or gene medicine development (antisense ODN or siRNA).
Figure 20:
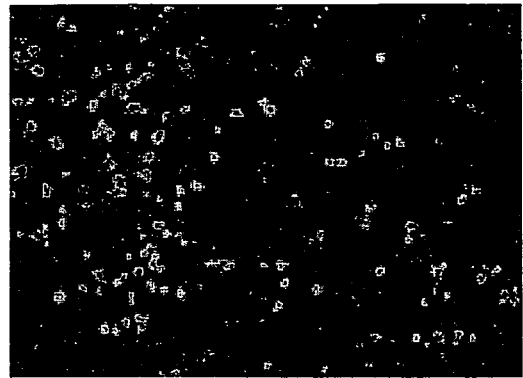
Figure 21:
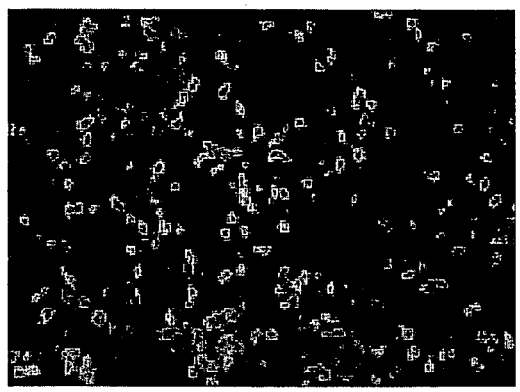
FIG. 21 illustrates a GFP reporter gene transfection assay in 923 cells with a transfectable glass slide system coated with cationic polymer (NDT-CP-1)-gelatin or cationic lipid (lipofectamine2000)-gelatin transfection mixture. The transfectable slide was loaded with GFP plasmid DNA by spotting 1-4 µl GFP plasmid (20 µg/ml) solution and allowing the slide to air dry. The glass slide was then put on the bottom of a six-well plate, followed by seeding 293 cells. The GFP signal was analyzed by fluorescent microscope. Only the areas spotted with GFP plasmid DNA showed green fluorescent signal, which indicated that the plasmid DNA was well affixed on the glass surface of spotted areas with transfection mixtures. The current technology is useful in transfection array applications, which could screen thousands of the target genes or gene medicine in cell based transfection assays for genomic function studies (cDNA library screening) or gene medicine development (antisense ODN or siRNA).
Figure 21:
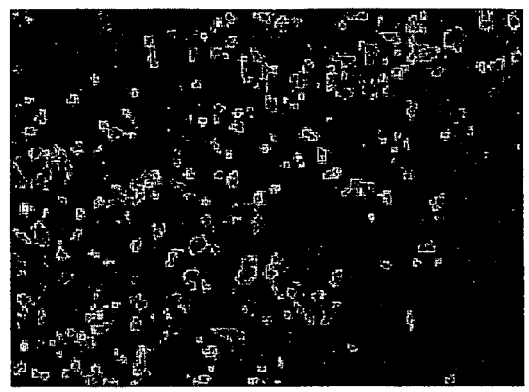

Making Transfectable Surface of Glass Slide by Spotting Transfection Reagent—Gelatin Mixture The 1-4 µl transfection/gelatin solution was spotted on a PLL coated slide. The slide was put on a clean hood for approximately 1 hour until completely dried. The dried slides were stored at 4° C. and ready for use (FIG. 20, 21).

Transfection Surface Prepared by Laminin Based Transfection Mixture

Laminin (Sigma, catalog # L2020) was diluted in PBS to a final concentration of 40.0 µg/ml and stored at 4° C.

Preparation of Transfection Mixture with Laminin

All transfection reagents were diluted in the 40.0 µg/ml laminin solution. The concentration of linear $PEI_{25k}$ and specially synthesized polymer samples ranged from 320.0 µg/ml to 40.0 µg/ml, and the concentration of branch $PEI_{25k}$ ranged from 160.0 µg/ml to 20.0 µg/ml. The concentration of Superfect ranged from 600.0 to 75.0 µg/ml, and lipofectamine concentration ranged from 200.0 µg/ml to 25.0 µg/ml. The concentration of polymers and lipid-polymer synthesized (NDT) ranged from 320.0 µg/ml to 40.0 µg/ml.

Making Transfectable Surface with 96 Well Plate and Transfection Reagent—Laminin Mixture The 25 µl transfection/laminin solution was added to each well of a 96 well plate. The plate was shaken for several seconds to make sure the entire bottom surfaces were cover by transfection/gelatin solution. Then the plate was allowed to air dry in a tissue culture hood for several hours (approximately 5-6 hours). The dried plate was stored at 4° C. and ready for use (FIG. 8-13).

Figure 22:
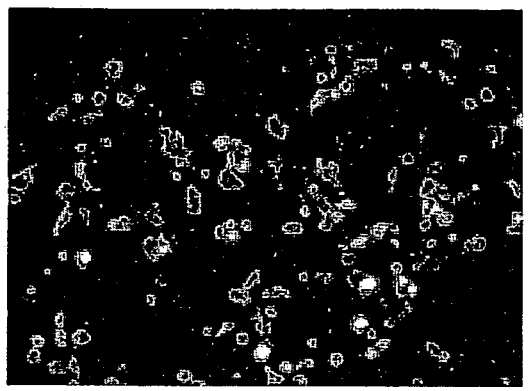
FIG. 22 illustrates a GFP reporter gene transfection assay in 923 cells with a transfectable glass slide system spotted with cationic polymer (NDT-CP-1)-laminin or cationic lipid (lipofectamine2000)-laminin transfection mixture. The transfectable slide was submerged in GFP plasmid solution. Although the whole slide was covered with GFP plasmid solution, only the cells that are on the spot where transfection mixtures were applied exhibited a GFP signal. This indicates that the transfection reagents were well affixed on the glass slide without diffusion. These results indicated that the current technology is useful in transfection array applications, which could screen thousands of the target genes or gene medicine in cell based transfection assays for genomic function studies or gene medicine development (antisense ODN or siRNA).
Figure 22:
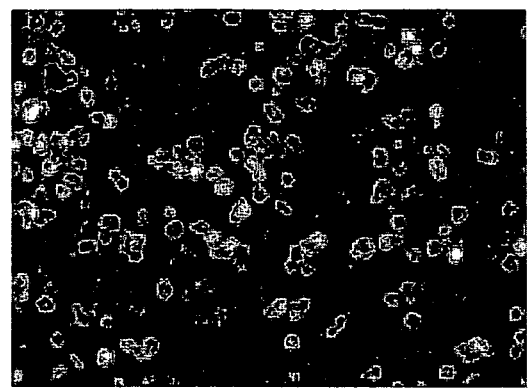
Figure 23:
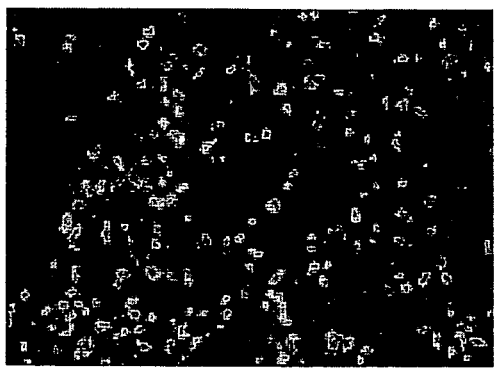
FIG. 23 illustrates a GFP reporter gene transfection assay in 923 cells with a transfectable glass slide system coated with cationic polymer (NDT-CP-1)-laminin or cationic lipid (lipofectamine2000)-laminin transfection mixture. The transfectable slide was loaded with GFP plasmid DNA by spotting 1-4 µl GFP plasmid (20 µg/ml) solution and allowing the slide to air dry. The glass slide was then put on the bottom of a six-well plate, followed by seeding 293 cells. The GFP signal was analyzed by fluorescent microscope. Only the areas spotted with GFP plasmid DNA showed green fluorescent signal, which indicates that the plasmid DNA was well affixed on the glass surface in the areas spotted with transfection mixtures. The current technology is useful in transfection array applications, which could screen thousands of the target genes or gene medicine in cell based transfection assays for genomic function studies (cDNA library screening) or gene medicine development (antisense ODN or siRNA).
Figure 23:
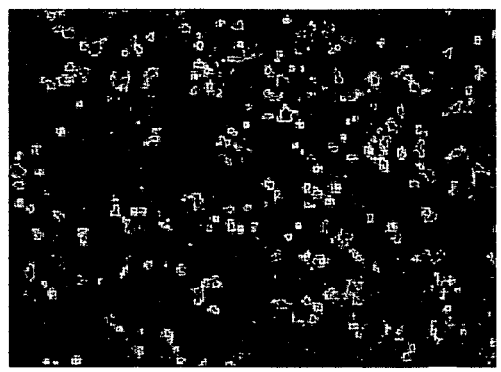

Making Transfectable Surface of Glass Slide by Spotting Transfection Reagent—Laminin Mixture The 1-4 µl transfection/gelatin solution was spotted on a PLL coated slide. The slide was placed on a clean hood for about 1 hour and allowed to dry completely. The dried slide was stored at 4° C. and ready for use (FIG. 22-23).

Transfection Surface Prepared by Collagen Based Transfection Mixture

Collagen (Sigma, catalog # C8919) was diluted in PBS to a final concentration of 120.0 µg/ml and stored at 4° C.

Preparation of Transfection Mixture with Laminin

All transfection reagents were diluted in the 120.0 µg/ml of collagen solution. The concentration of linear $PEI_{25k}$ and specially synthesized polymer samples ranged from 320.0 µg/ml to 40.0 µg/ml, and the concentration of branched $PEI_{25k}$ ranged from 160.0 µg/ml to 20.0 µg/ml. The concentration of Superfect ranged from 600.0 to 75.0 µg/ml, and lipofectamine concentration ranged from 200.0 µg/ml to 25.0 µg/ml. The concentration of polymers and lipid-polymer synthesized (NDT) ranged from 320.0 µg/ml to 40.0 µg/ml.

Figure 14:
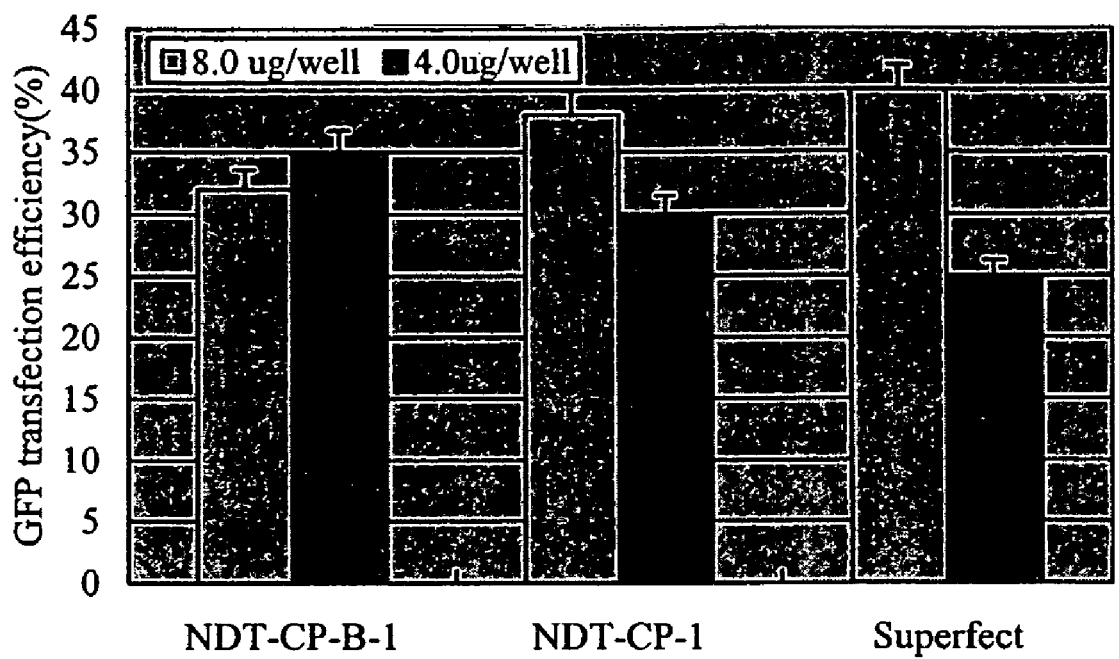
FIG. 14 illustrates the effect of using a transfectable surface coated with cationic polymer-collagen transfection mixture on GFP reporter gene transfection in 923 cells in a 96-well plate cell culture device system. The amounts of NDT-CP-1 and NDT-CP-B-1 is shown in the figure. The amounts of Superfect were 15 and 7.5 µg/well respectively. The GFP transfection efficiency mediated by cationic polymer-collagen transfection mixture system could reach up to 40%.
Figure 15:
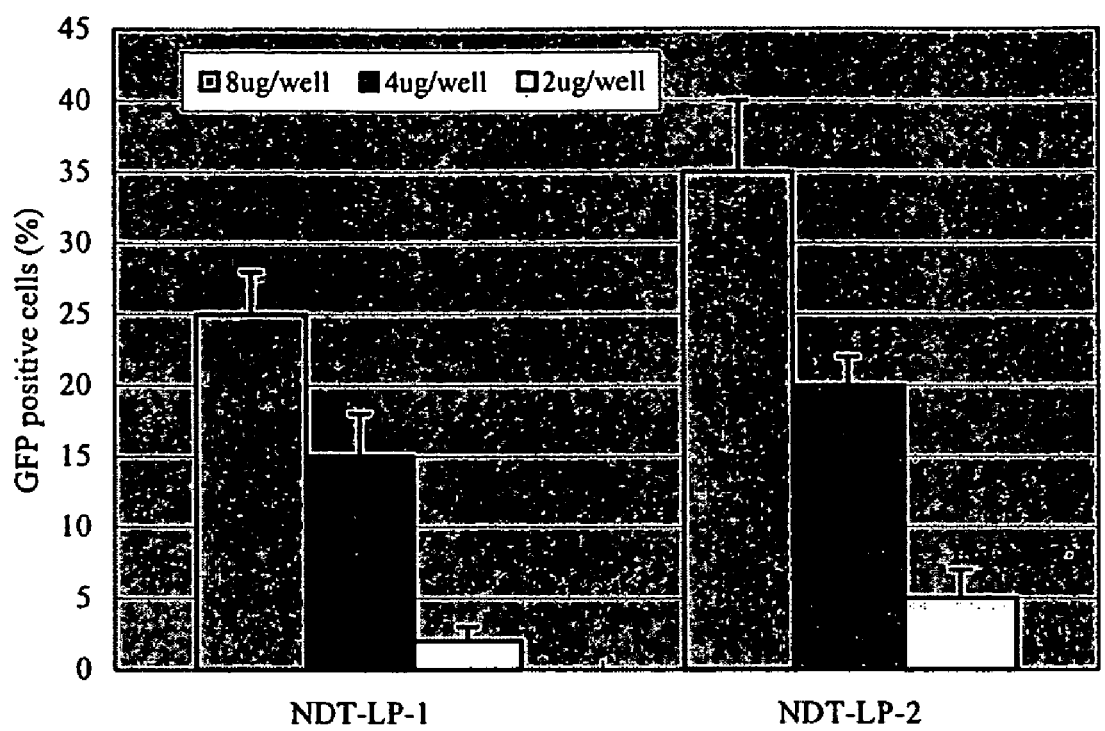
FIG. 15 illustrates the effect of using a transfectable surface coated with cationic lipid-polymer-collagen transfection mixture on GFP reporter gene transfection in 923 cells in a 96-well plate cell culture device system. The amount of lipid-polymer is shown as 8, 4, and 2 µg/well. The transfection efficiency mediated by cationic lipid-polymer-collagen transfection mixture system could reach up to 35%.
Figure 16:
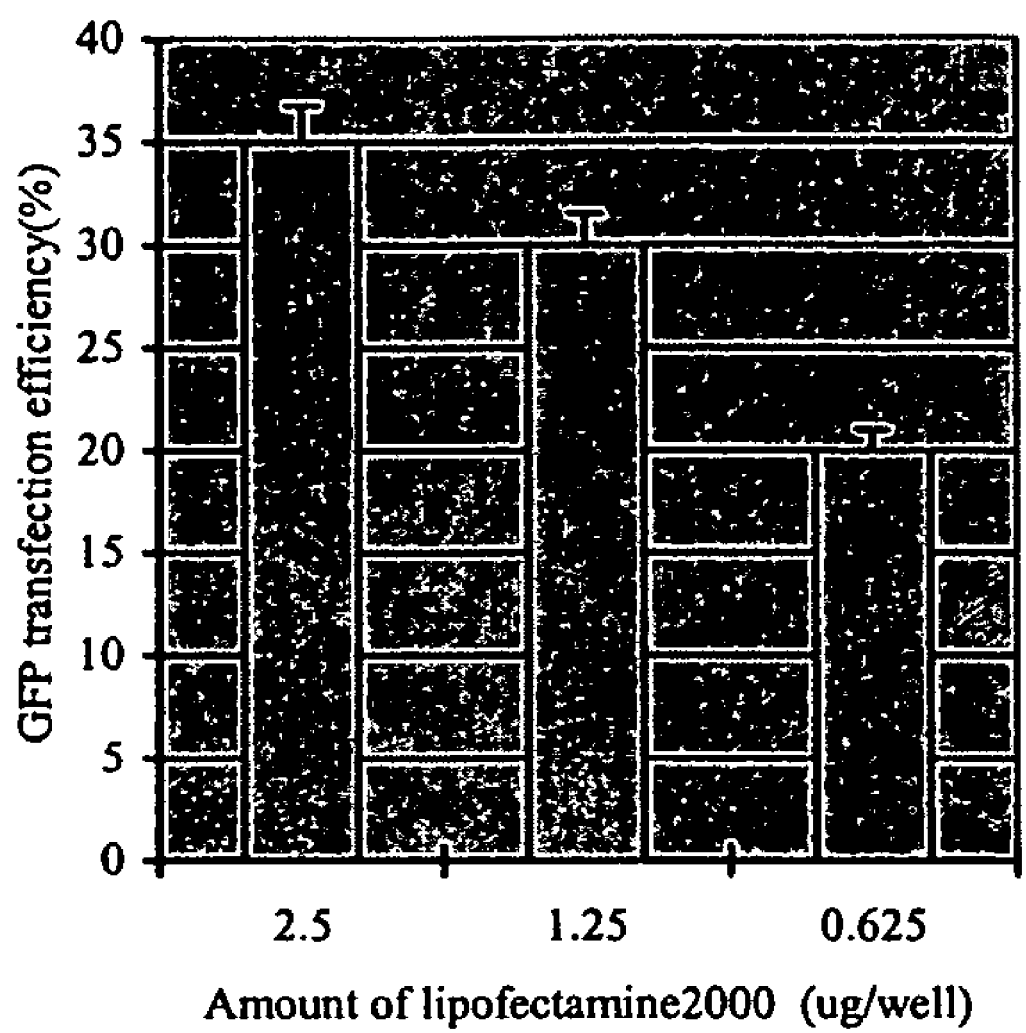
FIG. 16 illustrates the effect of using a transfectable surface coated with cationic lipid-collagen transfection mixture on GFP reporter gene transfection in 923 cells in a 96-well plate cell culture device system. The transfection efficiency mediated by cationic lipid-collagen transfection mixture system could reach up to 35%, similar to those mediated by lipofectamine 2000-gelatin transfection mixture system.

Making Transfectable Surface with 96 Well Plate and Transfection Reagent—collagen Mixture The 25 µl transfection/collagen solution was added to each well of a 96 well plate. The plate was shaken for several seconds to make sure the entire bottom surfaces were covered by transfection/gelatin solution. Then the plate was allowed to dry in a tissue culture hood for several hours (approximately 5-6 hours). The dried plate was stored at 4° C. and ready for use (FIG. 14-16).

Transfection Surface Prepared by Gelatin/Laminin Based Transfection Mixture

Laminin (Sigma, catalog # L2020) was diluted in 0.2% gelatin to a final concentration of 40.0 µg/ml and stored at 4° C.

Preparation of Transfection Mixture with Gelatin and Laminin

All transfection reagents were diluted in the 40.0 µg/ml laminin/0.2% gelatin solution. The concentration of linear $PEI_{25k}$ and specially synthesized polymer samples ranged from 320.0 µg/ml to 40.0 µg/ml, and the concentration of branch $PEI_{25k}$ ranged from 160.0 µg/ml to 20.0 µg/ml. The concentration of Superfect ranged from 600.0 to 75.0 µg/ml, and lipofectamine concentration ranged from 200.0 µg/ml to 25.0 µg/ml. The concentration of polymers and lipid-polymer synthesized (NDT) ranged from 320.0 µg/ml to 40.0 µg/ml.

Figure 17:
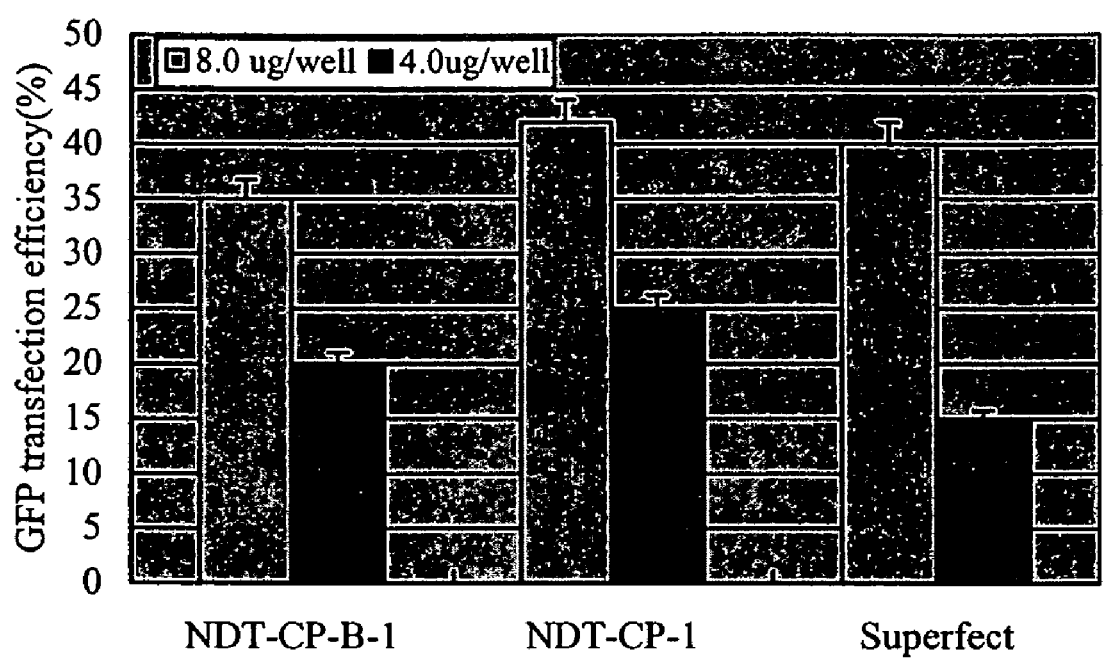
FIG. 17 illustrates the effect of using a transfectable surface coated with cationic polymer-gelatin-laminin transfection mixture on GFP reporter gene transfection in 923 cells in a 96-well plate cell culture device system. The amounts of NDT-CP-1 and NDT-CP-B-1 are shown in the figure. The amounts of Superfect were 15 and 7.5 µg/well respectively. The GFP transfection efficiency mediated by the cationic polymer-gelatin-laminin transfection mixture system could reach up to 42%.
Figure 18:
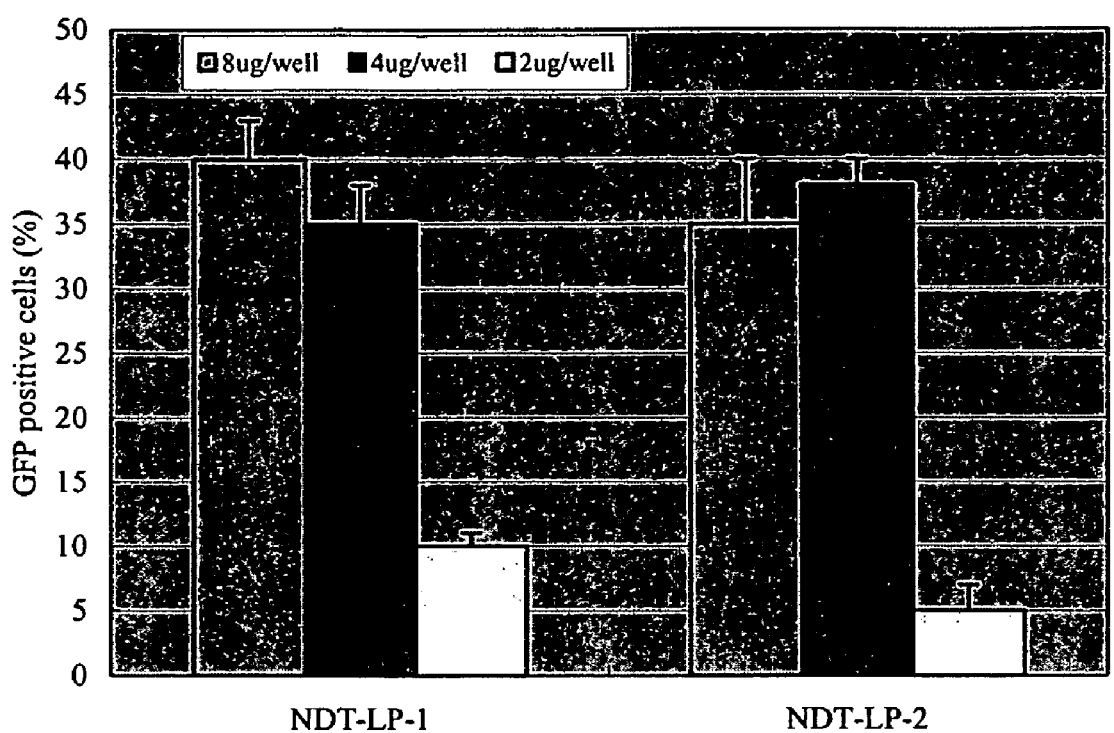
FIG. 18 illustrates the effect of using a transfectable surface coated with cationic lipid-polymer-gelatin-laminin transfection mixture on GFP reporter gene transfection in 923 cells in a 96-well plate cell culture device system. The amount of lipid-polymer is shown as 8, 4, and 2 µg/well. The GFP transfection efficiency mediated by the cationic lipid-polymer-gelatin-laminin transfection mixture system could reach up to 40%.
Figure 19:
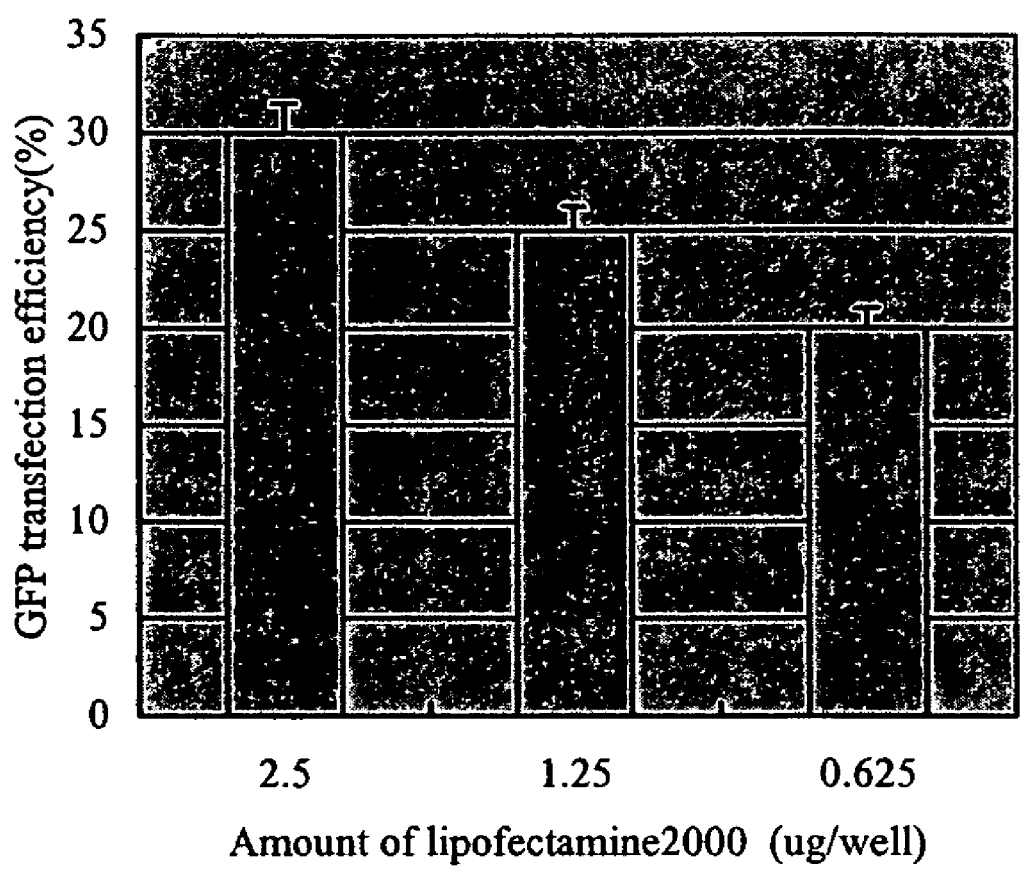
FIG. 19 illustrates the effect of using a transfectable surface coated with cationic lipid-gelatin-laminin transfection mixture on GFP reporter gene transfection in 923 cells in a 96-well plate cell culture device system. The transfection efficiency mediated by cationic lipid-gelatin-laminin transfection mixture system could reach up to 30%.

Making Transfectable Surface with 96 Well Plate and Transfection Reagent—Gelatin-Laminin Mixture The 25 µl transfection/gelatin/laminin solution was added to each well of a 96 well plate. The plate was shaken for several second to make sure the entire bottom surfaces were covered by transfection/gelatin solution. Then the plate was allowed to dry in a tissue culture hood for several hours (approximately 5-6 hours). The dried plate was stored at 4° C. and ready for use (FIG. 17-19).

Plasmid DNA Preparation

The plasmids pCMV-GFP and pCMV-luc were constructed according to standard DNA recombinant protocols. The expression of green fluorescent protein (GFP) and firefly luciferase gene cDNA was controlled by the human cytomegalovirus (CMV) promoter, and the transcripts were stabilized by a gene expression enhancer, chicken β-globulin intron. The plasmids were amplified in DH5α *E. coli* and purified with Qiagen Plasmid Max Preparation Kit according to the manufacturer's instruction. The quantity and quality of the purified plasmid DNA was assessed by spectrophotometric analysis at 260 and 280 nm, as well as by electrophoresis in 0.8% agarose gel. Purified plasmid DNA was dissolved in sterile ddH$_2$O and stored at −20° C.

Preparation of DNA Solution with DMEM pCMV-GFP or pCMV-luc plasmid was diluted in DMEM to a final concentration of 10 μg/ml. Thirty (30) μl DNA solution was added to the transfectable surface of 96-well plate or glass slide, and incubated at room temperature for 20-30 min.

Antisense Oligonucleotide Preparation

Luciferase 705 reporter gene system was developed by Dr. Kole in University of Northern Carolina (Kang S H et al. Biochemistry 1998; 37(18):6235-9). In this system, human β-globin with mutation at 705 was inserted into the sequence between luciferase cDNA. This plasmid was introduced into HeLa cell for stable gene expression; the cell line was termed as HeLa luc705. Usually the cells exhibit low luciferase activity, because the gene products (luciferases) with wrong splicing exhibit no activities. However, the antisense oligonucleotide binding to 705 sequence will block the wrong splicing site and produce luciferase protein with biological activity. Luciferase 705 is used as functional model for evaluation of the efficiency of antisense oligonucleotide delivery. Higher luciferase activity indicates higher efficiency of antisense delivery.

Figure 24:
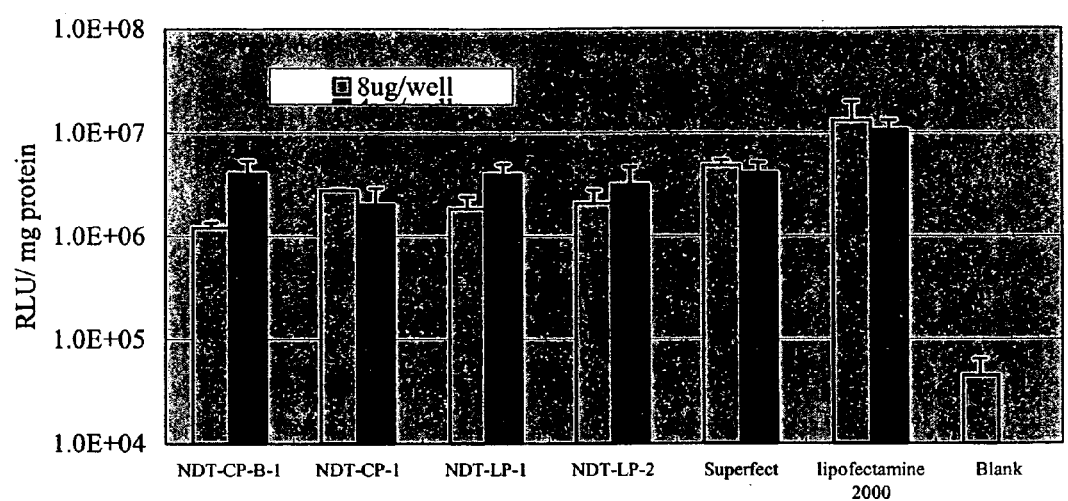
FIG. 24 illustrates the effect of using transfection reagent-laminin mixtures on antisense ODN transfection to Hela 705 Luc cells in a 96-well cell culture device. The results showed that transfectable surface composed of cationic polymer-laminin transfection mixture, lipid-polymer-laminin mixture, or lipid-laminin transfection mixture systems showed significant blocking of the target RNA, which suggested that not only plasmid, but also oligonucleotide could be successfully delivered into mammalian cells by this strategy.
Figure 25:
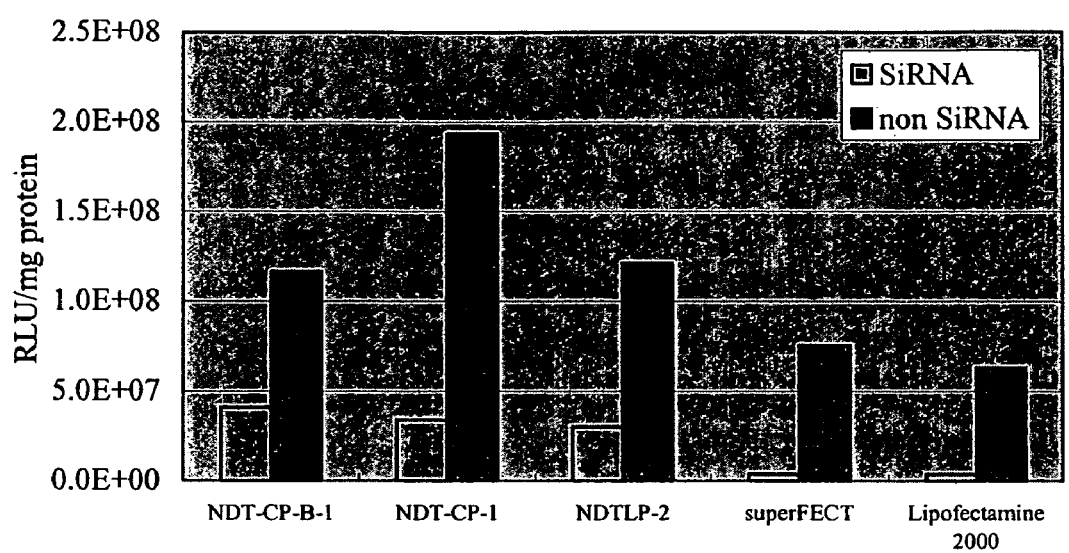
FIG. 25 illustrates the effect of using transfection reagent-laminin mixtures on siRNA delivery to 293 cells in a 96-well cell culture device. In comparison to the non-siRNA control group, transfectable surfaces composed of cationic polymer-laminin transfection mixture, lipid-polymer-laminin mixture, or lipid-laminin transfection mixture systems showed significant blocking of the target RNA, which suggested that not only plasmid, but also siRNA could be successfully delivered into mammalian cells by this strategy.

In present studies, the 18nt 2'-O-methyl-phosphorothioate oligonucleotide binding to luc705 sequence was synthesized. The sequence is CCUCUUACCUCAGUUACA (SEQ ID NO: 1). The antisense oligo was diluted in optimal MEM, final concentration was 0.6 μmol/L. 30 μl of antisense oligo was add to the transfectable surface of each well described previously and incubated at room temperature for 25 min (FIG. 24).

siRNA Preparation siRNA is a double stranded RNA fragment with 21 to 25 bp, which can bind and destroy target mRNA and lead to down regulation of gene expression levels. In this experiment, the luciferase plasmid and siRNA synthetic cassette which targets luciferase gene were prepared in opti MEM and were added into the transfectable plate described previously and incubated for 25 min. The amounts of luciferase plasmids were 0.5 μg/well and siRNA synthetic cassettes were about 0.5 μg/well (FIG. 25).

Tat Peptide Delivery

Figure 26:
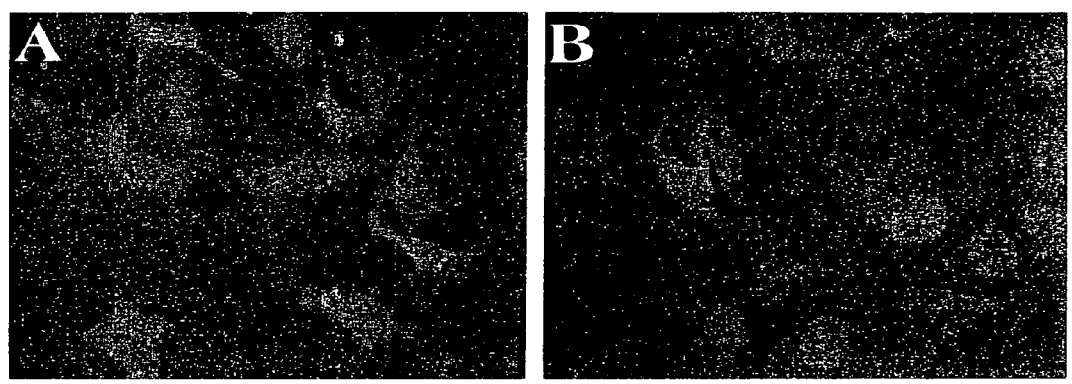
FIG. 26 illustrates typical results of Tat peptide signal in HeLa cells.

Biotin labeled Tat peptide of various concentrations (50, 25, 12.5 and 6.3 μg/well) were prepared with 0.2% gelatin solution and coated on a 96 well plate, respectively. The plate was dried by sitting in a cell culture hood for several hours. 1.5×10$^4$ HeLa cells/well were seeded on the plate coated with peptide and incubated at 37° C. for 4 h. The cells were fixed with 0.2% glutaraldehyde/PBS for 5 min followed by treatment with 10% methanol. After being blocked with 10% serum at 37° C. for 30 min, the cells were incubated with streptavidin-FITC at 37° C. for 30 min. The cells were washed with PBS and the fluorescent signal was observed under a fluorescent microscope. If the peptide were successfully delivered into cells, the biotin-conjugated peptide can specifically bind to strreptavidin-FITC and lead to peptides be able to produce fluorescent signals. The increased FITC signal in cells indicates that more peptides were transported into the cells (FIG. 26).

The Effect of Targeting Moiety in Transfection Mixture on Transfectable Surface System Mediated Gene Transfer Transferrin Conjugated Poly-L-Lysine Preparation Transferrin can be absorbed by liver cells in a transferrin receptor mediated endocytosis pathway. Transferrin has been successfully reported as cell targeting molecular that could improve gene delivery efficiency in liver cells (Wagner E, Ogris M, Zauner W. Adv Drug Deliv Rev 1998; 30(1-3):97-113).

Figure 27:
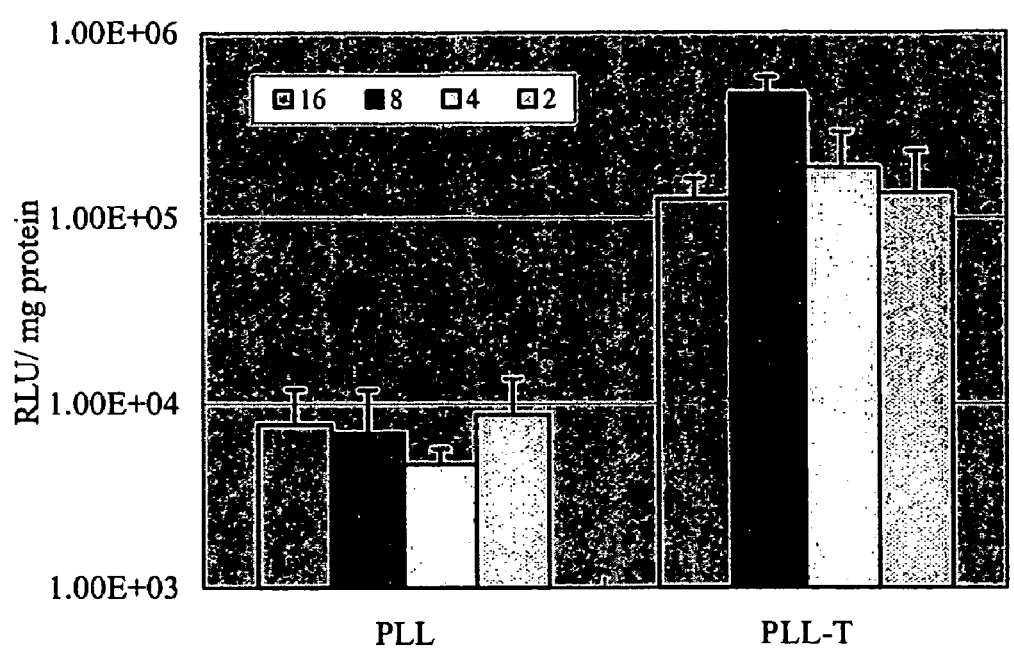
FIG. 27 illustrates the effect of a targeting molecule (transferring) on cationic polymer (PLL)-laminin transfection mixture mediated gene transfer in HepG2 cells with transfectable surface technology in a 96-well cell culture device system. The results indicate that introduction of targeting molecules (transferring) in PLL-laminin based transfectable surface systems could significantly enhance transfection efficiency.

Effect of Targeting Molecule (Transferrin) on Cationic Polymeric Transfection Reagent Mediated Gene Transfer in Laminin-Based Transfection Mixture System In this experiment, 25 μl of poly-L-lysine conjugated with transferrin (PLL-T) was coated on a 96 well plate with 40.0 μg/ml laminin. Poly-L-lysine (PLL) was used as a control. The ranges of concentration of PLL-T and PLL are from 320.0 μg/ml to 40.0 μg/ml. After air drying, 25 μl luciferase plasmid solution (20.0 μg/ml, with the polymer/DNA ratio of 16:1 to 2:1.) was added into the plate and incubated at room temperature for 25 min. The dried plate was ready to use in related experiments (FIG. 27).

Effect of Membrane-Destabilizing Component in Transfection Mixture on Transfectable Surface System Mediated Gene Transfer VSVG is a viral envelope protein with membrane-destabilizing properties resulting in membrane fusion and disruption of the membranes of the cell. VSVG has been used as a gene transfection enhancer which can dramatically increase the cationic polymer (PLL) mediated gene transfection. A peptide from the cell fusion domain of VSVG protein was synthesized. The sequence of this peptide is RRRQGTWLNPG-FPPQSCGYATVTDARRR (SEQ ID NO: 2), with the amino acid arginine at the end of the C and N terminal respectively in order to improve the solubility of the peptide.

Figure 28:
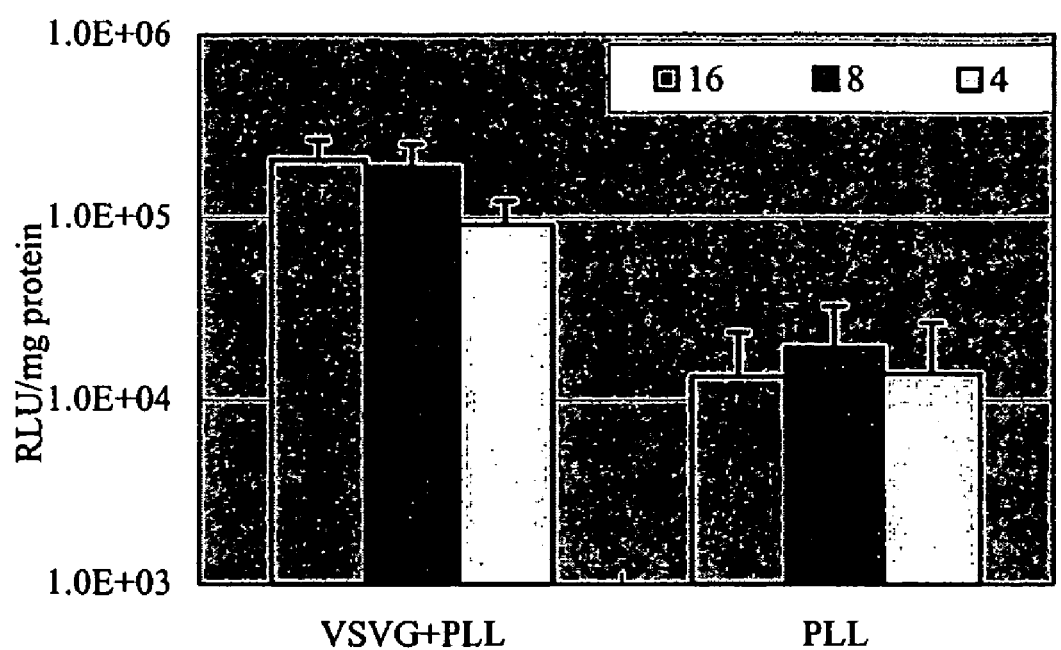
FIG. 28 illustrates the effect of membrane disturbing peptide (VSVG peptide) on cationic polymer (PLL)-laminin transfection mixture mediated gene transfer in 293 cells with transfectable surface technology in a 96-well cell culture device system. The results indicate that introduction of membrane disturbing peptide (VSVG peptide) in PLL-laminin based transfectable surface systems could significantly enhance transfection efficiency.

VSVG peptide and poly-L-lysine were diluted in 40.0 μg/ml laminin. The concentration of VSVG peptide was 1.0 mg/ml, and the concentration of PLL ranged from 640 μg/ml to 160.0 μg/ml. In the control group only PLL was diluted in laminin solution at same concentration. 25 μl of the PLL or PLL+VSVG peptide solution was added into 96 well plate and let it air dry. The amount of PLL was 16.0, 8.0 and 4.0 μg/well respectively (FIG. 28).

Figure 32:
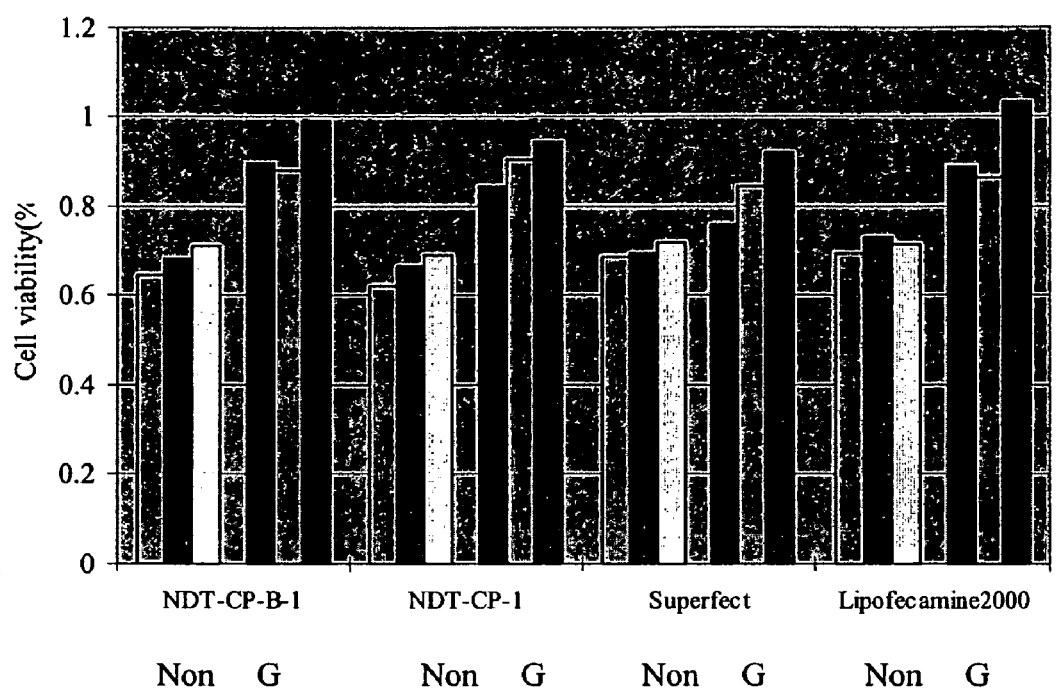
FIG. 32 illustrates the effect of introduction of cytoreductive reagents (glutamine) in a transfection reagents-laminin based transfectable surface on cytotoxicity improvement in 293 cells. The "Non" indicates samples without glutamine, and "G" indicates samples with glutamine. The results showed that glutamine (cytoreductive reagent) significantly improved transfection cytotoxicity compared to that without glutamine group, which indicated that cytoreductive reagents are excellent candidates for reducing cytotoxicity caused by transfection reagents and transfection procedures.

Effect of Cytoreductive Reagent in Transfection Mixture on Transfectable Surface System Mediated Gene Transfer Glutamine is a cytoreductive reagent which can protect cells against ammonia-induced cytotoxicity (Nakamura E and Hagen S J. Am J Physiol Gastointest liver Physiol 283 G1264-1275, (2002)). Since almost all cationic polymers or cationic lipids contain amine groups, the addition of glutamine into the transfection mixture for transfectable surface preparation plays a role in protection against the cytotoxicity of transfection. Glutamine (100 mmol/L) and different transfection reagents (NDT-CP-B-1, NDT-CP-1, Superfect and lipofectamine 2000) were diluted in 0.2% gelatin solution, and 25 μl of the solution containing Glutamine/transfection reagent/gelatin was added into a 96 well plate and allowed to air dry. Then 25 μl GFP plasmid solution in opti MEM (20.0 μg/ml) was added into each well and incubated at room temperature for 25 min. The dried plate was ready for use (FIG. 32).

Figure 33:
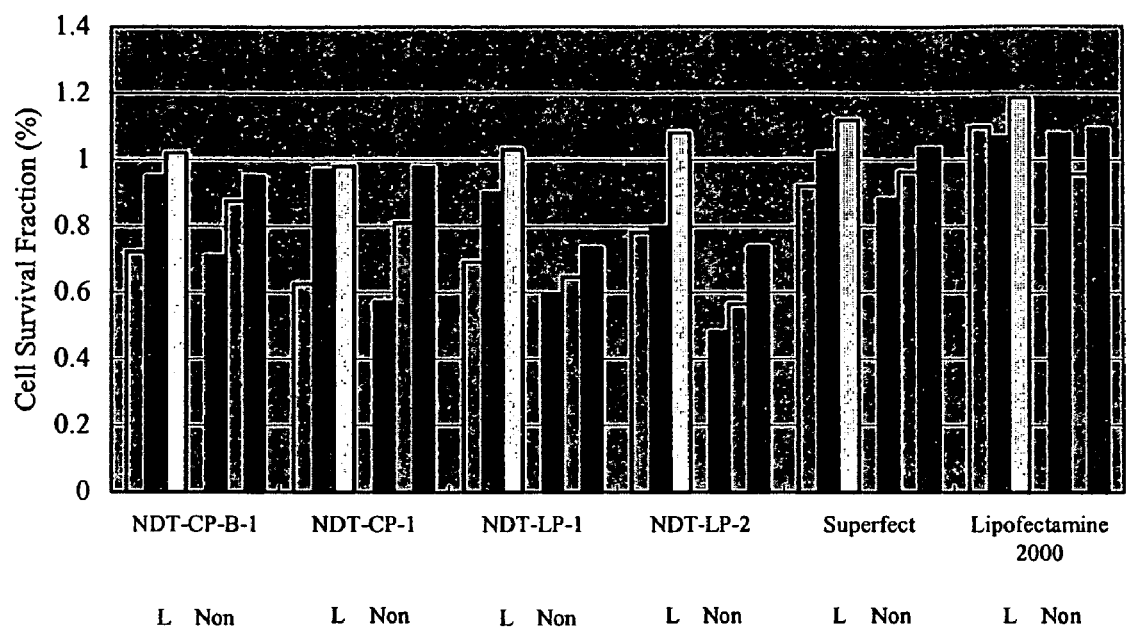
FIG. 33 illustrates the effect of introduction of cell attaching reagents and cell stimulating reagent (laminin) in a transfection reagents-gelatin based transfectable surface on cytotoxicity improvement to 293 cells. "L" indicates samples with laminin and "Non" indicates samples without laminin. The results indicate that the cell attaching reagent, such as laminin, significantly improved cytotoxicity caused by transfection reagents and transfection procedures in a transfectable surface technology system.

The Effect of Cell Attaching Reagent in Transfection Mixture on Transfectable Surface System Mediated Gene Transfer Laminin is a matrix for support cell growth and differentiation. Laminin is a commonly used cell attaching reagent. In this experiment, 0.2% gelatin or 0.2% gelatin and 40.0 μg/ml laminin mixture was used for diluting transfection reagents NDT-CP-B-1, NDT-CP-1, NDT-LP-1 NDT-LP-2, Superfect and lipofectamine 2000, and 25 μl solution was added into 96 well plate. The amounts of NDT polymers used in each well were 8, 4 or 2 μg, respectively, the amounts of Superfect were 15, 7.5 and 3.8 μg/well respectively, and the amounts of lipofectamine 2000 were 2.5, 1.25 and 0.63 μg/well respectively. After air drying, 25 μl of GFP plasmid in Opti MEM (20 μg/ml) was added into each well and incubated at room temperature for 25 min, then 5×10⁴ 293 cells/well were seeded in the plate. The cells were further incubated at 37° C. for 24 hours. The transfection efficiency and cytotoxicity were analyzed by fluorescent microscope and MTT assay (FIG. 33).

Cell Culture

HEK 293T cells was maintained in DMEM (Gibco) containing 10% fetal bovine serum, 100 units/ml penicillin and 100 μg/ml streptomycin. In this media the cells had a doubling time of about 20 hours, and the cells were split every 3-4 days to avoid over confluency.

HeLa 705 cell line was from Human cervical carcinoma HeLa cells after introducing firefly luciferase gene with a mutant β-globin intron (a mutation at 705 position) which results in a mutated luciferease protein due to the incorrect splicing. However, the mutated intron can be corrected by a specific antisense oligo nucleotide after it blocks the wrong splicing site (Kang S H et al. Biochemistry 1998; 37(18): 6235-9). The cell line was maintained in DMEM (Gibco) containing 10% fetal bovine serum, 100 units/ml penicillin and 100 μg/ml streptomycin. 200 μg/ml hygromycin was added into medium to maintain the luc-705 plasmid. In this media the cells had a doubling time of about 20 hours, and the cells were split every 3-4 days to avoid over confluency.

Human liver tumor cell line HepG2 was maintained in α-MEM medium (Gibco) containing 10% fetal bovine serum, 100 units/ml penicillin and 100 μg/ml streptomycin. In this media the cells had a doubling time of about 20 hours, and the cells were split every 3-4 days to avoid over confluency.

Figure 29:
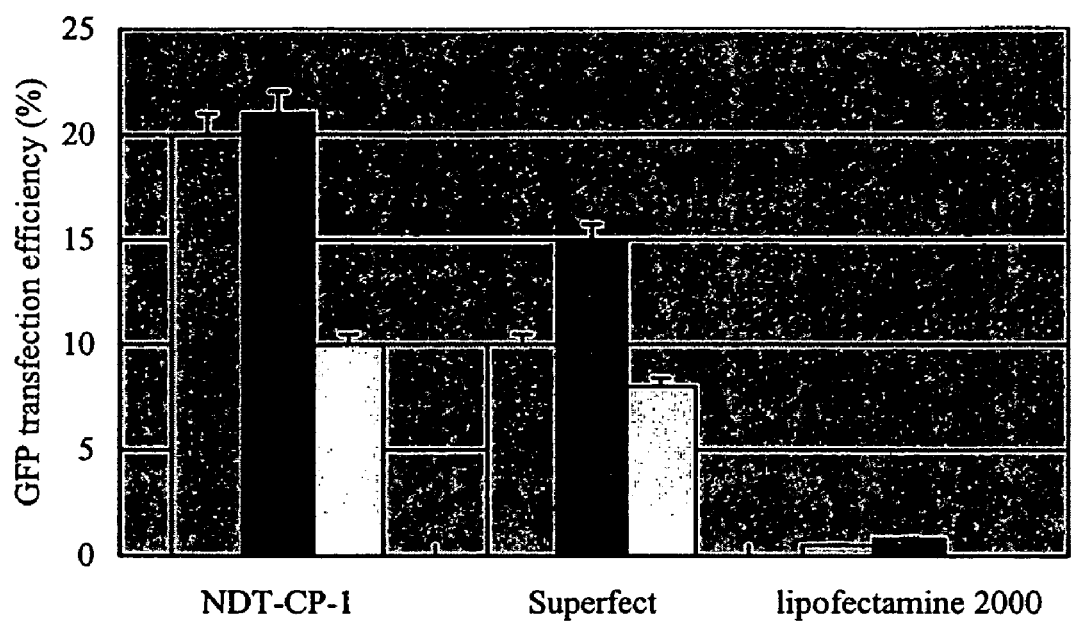
FIG. 29 illustrate the effect of using transfection reagent-laminin mixtures in GFP reporter gene delivery to HUV-EC cells in a 96-well cell culture device. The GFP transfection efficiency of NDT-CP-1 was about 20%, and the efficiency of Superfect was about 15%. The lipofectamine showed very low transfection efficiency (<1.0%). It indicated that not only transformed cell lines, such as 293, HeLa, HepG2 could be transfected, but also primary cells could be transfected by cationic polymer-laminin transfection mixture systems.
Figure 30:
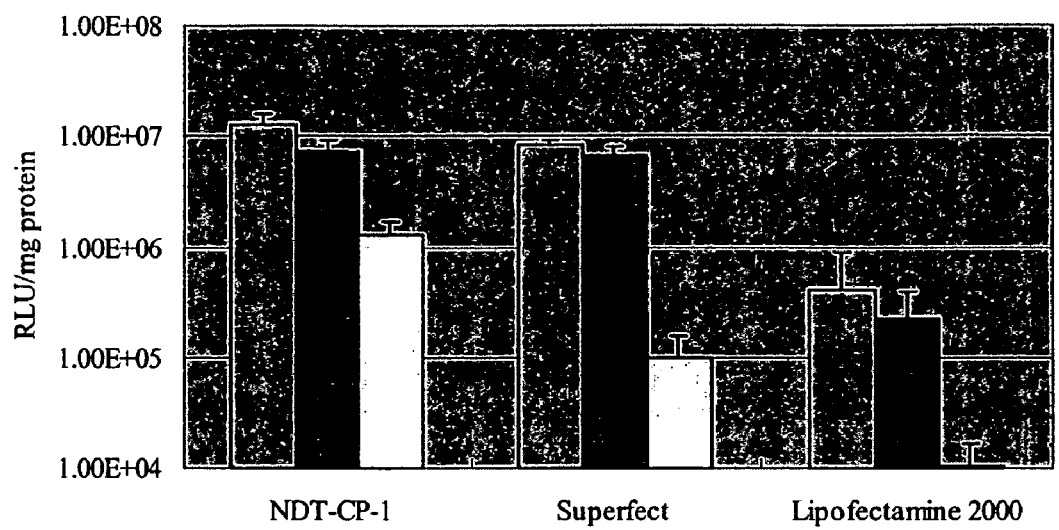
FIG. 30 illustrates the effect of transfection reagent-laminin mixtures on luciferase reporter gene delivery to HUV-EC cells in a 96-well cell culture device. The transfection efficiency of NDT-CP-1 and Superfect transfection efficiency were $1.26 \times 10^7$ and $8.26 \times 10^6$ RLU/mg protein respectively. Lipofectamine 2000 showed lower efficiency compared to the cationic polymer-laminin mixture system. This further confirmed that primary cells could be transfected with different gene according to embodiments of the present invention.

Human primary endothelial cell HUV-EC cell line was grew and maintained in EBM medium (Cambrex Corp.) containing 10% fetal bovine serum, 100 units/ml penicillin and 100 μg/ml streptomycin, and different types of growth factors according to the manufacturers instructions (FIG. 29-30).

Cell Preparation and Seeding onto the Transfectable Surface

Immediately prior to transfection, in a tissue culture hood, cells were harvested from a 10 cm dish as follows:
a. Media was removed, cells were rinsed with 2 ml of PBS, the solution was allowed to spread over the plate and then the solution was removed immediately.
b. 0.5 ml trypsin-EDTA was added to the cells and evenly spread over plate and the trypsin-EDTA was then immediately removed.
c. The cells were allowed to sit in the hood for 3-5 minutes. The plate was then agitated to dislodge cells from the surface of the plate.
d. Six (6) ml of 37° C. full medium was added to the plate of cells, and the solution was pipetted up and down 12-15 times with a 10 ml pipette until a single cell suspension was obtained, while avoiding the creation of too much froth. Another 14 ml of medium was added and the cells were completely suspended in the solution.
e. Cells were quantified in a hemocytometer.
f. The HEK 293T, HepG2 cells were diluted to a final concentration of 4-5×10⁵ cell/well in a sterile basin, and 100 μl (4-5×10⁴ cells) were be seeded for each well in a 96-well plate. The optimal concentration of HeLa 705 and HUV-EC cells were 1-2×10⁵ cell/ml.

GFP Reporter Gene Transfection Assay

Green fluorescent protein (GFP) gene was used in an initial screening. After transfection, the GFP signal in cells was observed under fluorescent microscope (Olympus, filter 520 nm). Cells were photographed using a 10× objective. The percentage of cells with GFP signal in transfected cultures was determined from counts of three fields for optimal cationic polymer amounts.

Luciferase Assay

Measurement of luciferase activity was performed using a chemiluminescent assay following the manufacturer's instructions (Luciferase Assay System; Promega, Madison, Wis., USA). Briefly, thirty hours after gene transfer, the cells were rinsed twice with PBS and then were lysed with lysis buffer (1% Triton X-100, 100 mM $K_3PO_4$, 2 mM dithiothreitol, 10% glycerol, and 2 mM EDTA pH 7.8) for 15 min at room temperature. A 10-μl aliquot of cell lysate was then mixed with 50-μl of luciferase assay reagent with an injector at room temperature in the luminometer. Light emission was measured in triplicate over 10 seconds and expressed as RLUs (relative light units). Relative light units (RLU) were normalized to the protein content of each sample, determined by BSA protein assay (Pierce, Rockford, Ill.). All the experiments were conducted in triplicate.

Cytotoxicity Assay-MTT Assay

Figure 31:
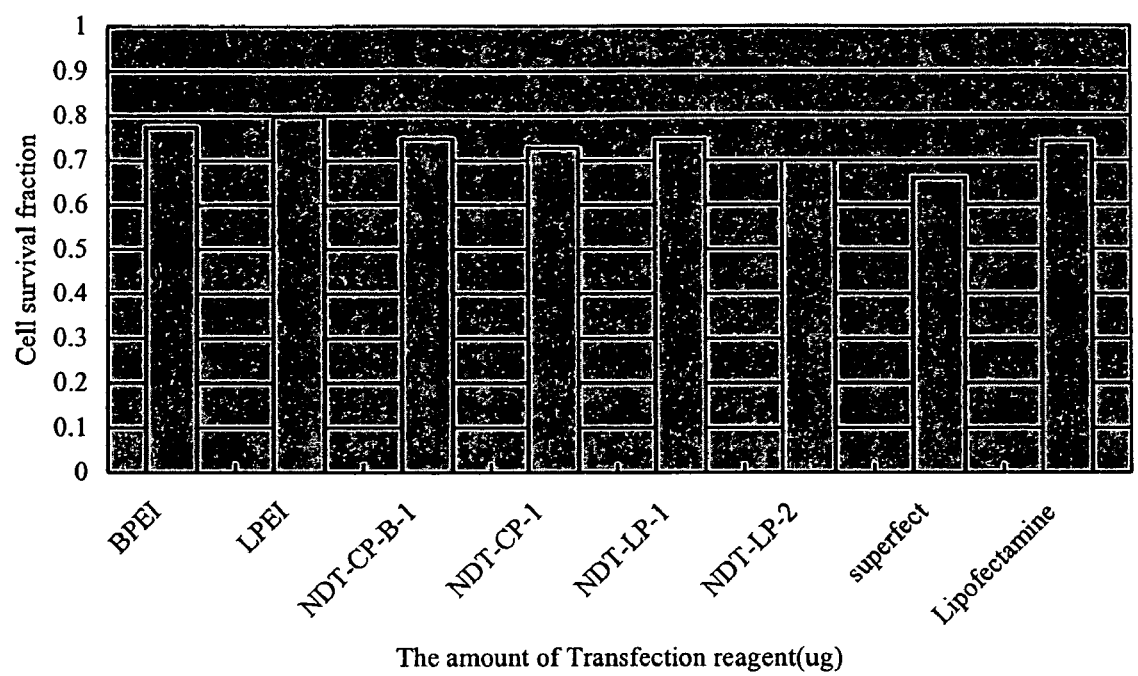
FIG. 31 illustrates the cell survival fraction of 293 cells after transfection in a 96 well plate coated with transfection reagent-gelatin. All samples showed a high survival fraction (>65%). It indicates that the cytotoxicity of transfection reagents used according to methods described herein are acceptable.

The cytotoxicities of transfection reagents on mammalian cells were evaluated using 3-[4,5 dimethylthiazol-2-yl]-2,5-diphenyltetrazolium bromide (MTT) method. Forty (40) hours after transfection, 10 μl of MTT solution (5.0 mg/ml, Sigma) was added to each well, and incubated for 3 hrs. The medium was then removed and 200-μl DMSO was added to dissolve the formazan crystals. The absorbance of the solution was measured at 570 nm. Cell viabilities was calculated using the equation: Viability (%)={$Abs_{570\ (sample)}$/$Abs_{570\ (control)}$}×100 (FIG. 31).

Stability Study

Figure 34:
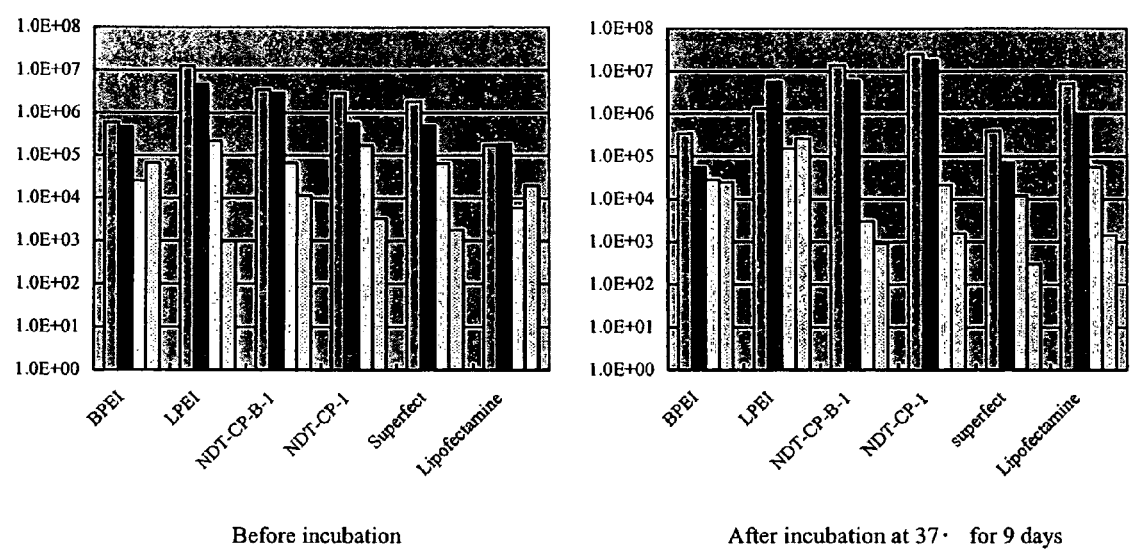
FIG. 34 illustrates an evaluation of shelf-life of transfectable surfaces in stability studies. The results showed that there are no significant differences in transfection performances in flash-made transfectable surfaces or that with the treatment at 37° C. for 9 days, which indicated that the shelf life of transfectable surface could be 1.5 years when stored at 4° C.

LPEI, BPEI, NDT-CP-B-1, NDT-CP-1, Superfect and lipofectamine in 0.2% gelatin were coated in 96-well plate as described previously. After air-drying, the plate was incubated at 37° C. for 9 days. The plate was then ready for use. 25 μl/well luciferase plasmid (20.0 μg/ml in optimal MEM) was added to the plates (before and after 37° C. incubation) and incubated for 25 min. 5×10⁴ 293 cells were seed in the plate and incubated at 37° C. for 48 hours. The gene transfection efficiency of the transfectable surface of the flash plate or of 37° C. incubation for 9 days was compared (FIG. 34).

While this invention has been particularly shown and described with references to preferred embodiments thereof, it will be understood by those skilled in the art that various changes in form and details may be made therein without departing from the scope of the invention. All references cited herein are incorporated herein by reference.

What is claimed is:

1. A substrate for receiving both nucleic acid and eukaryotic cells, the substrate consisting of:
   a support, the support being coated only with a mixture that consists of polyethylenimine (PEI) and a biocompatible biopolymer, or a mixture of PEI, a transferrin-linked PEI, and a biocompatible biopolymer,
wherein the substrate is free of nucleic acid of interest and the PEI captures, and thereby facilitates adhesion onto the substrate, both nucleic acid and eukaryotic cells in a solution.

2. The substrate of claim 1, wherein the mixture of the PEI and the biocompatible biopolymer is homogenously and non-covalently disposed on the surface of the support.

3. The substrate of claim 2, wherein the cells are mammalian cells.

4. The substrate of claim 1, wherein the mixture of the PEI, the transferrin-linked PEI, and the biocompatible biopolymer is homogenously and non-covalently disposed on a surface of the support.

5. The substrate of claim 4, wherein the cells are mammalian cells.

6. The substrate of claim 1, wherein the cells are mammalian cells.

7. A method of introducing nucleic acid into eukaryotic cells, the method comprising:
   providing a substrate according to claim 1, and,
   contacting the mixture of the PEI and the biocompatible biopolymer, or the mixture of the PEI, the transferrin-linked PEI, and the biocompatible biopolymer with nucleic acid and eukaryotic cells, whereby both the nucleic acid and the eukaryotic cells adhere to the PEI on the substrate.

8. The method of claim 7, wherein the cells are mammalian cells.

9. The method of claim 7, wherein the contacting step is performed by contacting the mixture of the PEI and the biocompatible biopolymer, or the mixture of the PEI, the transferrin-linked PEI, and the biocompatible biopolymer with the nucleic acid and the cells in vitro.

10. The method of claim 7, wherein the contacting step is performed by first contacting the mixture of the PEI and the biocompatible biopolymer, or the mixture of the PEI, the transferrin-linked PEI, and the biocompatible biopolymer with the nucleic acid in vitro and then with the cells in vivo.

11. A transfection device comprising a substrate consisting of a support coated with a mixture that consists of polyethylenimine (PEI) and at least one additional compound selected from the group consisting of gelatin, collagen, albumin, and laminin and/or a cell targeting agent which is transferrin.

12. A method of introducing nucleic acid into eukaryotic cells comprising:
   providing a transfection device according to claim 11;
   applying the nucleic acid to the transfection device; and
   introducing the eukaryotic cells.

13. A method for introducing nucleic acids into eukaryotic cells comprising: (a) providing a substrate according to claim 1, (b) adding the nucleic acids to be introduced into the eukaryotic cells onto the substrate, (c) seeding cells on the substrate at a sufficient density and under appropriate conditions for introduction of the nucleic acids into the eukaryotic cells.

14. The method of claim 13, wherein the support is selected from the group consisting of flasks, dishes, multi-well plates, glass slides, and implanted devices.

15. The method of claim 13, wherein said substrate is prepared by evenly spreading the mixture of the polyethylenimine (PEI) and the biocompatible biopolymer, or the mixture of the PEI, the transferrin-linked PEI, and the biocompatible biopolymer on the substrate or spotting said mixture of the PEI and the biocompatible biopolymer, or the mixture of the PEI, the transferrin-linked PEI, and the biocompatible biopolymer in discrete areas of the substrate.

16. The method of claim 13, wherein said biocompatible polymer is selected from gelatin, collagen, laminin, fibronectin, and bovine serum albumin or a mixture thereof.

17. The method of claim 13, wherein said biocompatible polymer is selected from hydrogels, biodegradable polymers, and biocompatible materials.

18. The method of claim 13, wherein the eukaryotic cells are mammalian cells.

19. The method of claim 18, wherein the mammalian cells are dividing cells or non-dividing cells.

20. The method of claim 18, wherein the mammalian cells are transformed cells or primary cells.

21. The method of claim 18, wherein the mammalian cells are somatic cells or stem cells.

22. The method of claim 13, wherein the eukaryotic cells are plant cells.

23. The method of claim 13, wherein said substrate is prepared by an automated mechanism.

24. The method of claim 13, wherein the nucleic acid is selected from the group consisting of DNA, RNA, and DNA/RNA hybrid.

25. The method of claim 13, wherein the nucleic acid is selected from the group consisting of a linear molecule, a plasmid, and single stranded oligodeoxynucleotide (ODN).

26. The method of claim 13, wherein the nucleic acid is selected from the group consisting of single stranded RNA (ribozyme) or double stranded RNA (siRNA).

27. The method of claim 13, wherein the eukaryotic cells are insect cells.

28. The method of claim 13, wherein the substrate is prepared manually or by an automated mechanism.

29. A method of determining whether a nucleic acid can enter a cell comprising (a) providing a substrate according to claim 1 to which said nucleic acid can interact, (b) adding the nucleic acid to the substrate such that the nucleic acid interacts with said mixture of the PEI and the biocompatible biopolymer, or the mixture of the PEI, the transferrin-linked PEI, and the biocompatible biopolymer, (c) seeding cells onto the substrate with sufficient density and under appropriate conditions for introduction of the nucleic acid into the cells, and (d) detecting whether the nucleic acid has been delivered to the cells.

30. The method of claim 29 wherein the nucleic acids is selected from the group consisting of DNA, RNA, and DNA/RNA hybrid.

31. The method of claim 30 wherein the nucleic acids is selected from the group consisting of a linear molecule, a plasmid, and single stranded oligodeoxynucleotide (ODN).

32. The method of claim 30, wherein the nucleic acids is selected from the group consisting of single stranded RNA (ribozyme) or double stranded RNA (siRNA).

33. The method of claim 29, wherein the eukaryotic cells are mammalian cells.

34. The method of claim 33, wherein the mammalian cells are dividing cells or non-dividing cells.

35. The method of claim 33, wherein the mammalian cells are transformed cells or primary cells.

36. The method of claim 33, wherein the mammalian cells are somatic cells or stem cells.

37. The method of claim 29, wherein the cells are selected from the group consisting of plant, insect, and bacterial cells.

38. The method of claim 29, wherein said detecting is performed by detecting said nucleic acid, a product of the nucleic acid, or activity of the product of the nucleic acid.

* * * * *

UNITED STATES PATENT AND TRADEMARK OFFICE
CERTIFICATE OF CORRECTION

PATENT NO. : 8,192,989 B2
APPLICATION NO. : 11/527134
DATED : June 5, 2012
INVENTOR(S) : Yu et al.

It is certified that error appears in the above-identified patent and that said Letters Patent is hereby corrected as shown below:

Page 1, Column 2, Line 53, Other Publications, "Polyethyenimine,"" should be changed to --Polyethylenimine,"--

Column 7, Line 4, "to Hela 705" should be changed to --to HeLa 705--

Column 11, Line 25, "into the transfction" should be changed to --into the transfection--

Column 11, Line 33, "on descrete locations" should be changed to --on discrete locations--

Column 15, Line 58, "bind to strreptavidin-FITC" should be changed to --bind to streptavidin-FITC--

Column 16, Line 41, "Gastointest liver" should be changed to --Gastrointest liver--

Column 17, Line 16, "mutated luciferease protein" should be changed to --mutated luciferase protein--

Signed and Sealed this
Twenty-third Day of October, 2012

David J. Kappos
*Director of the United States Patent and Trademark Office*